(12) United States Patent
Miles et al.

(10) Patent No.: US 8,598,117 B2
(45) Date of Patent: *Dec. 3, 2013

(54) PESTICIDAL TOXINS

(75) Inventors: Paul J. Miles, Research Triangle Park, NC (US); Vance Cary Kramer, Research Triangle Park, NC (US); Shen Zhicheng, Morrisville, NC (US); Frank Arthur Shotkoski, Cary, NC (US); Gregory W. Warren, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 69 days.

This patent is subject to a terminal disclaimer.

(21) Appl. No.: 13/542,775

(22) Filed: Jul. 6, 2012

(65) Prior Publication Data

US 2012/0270776 A1   Oct. 25, 2012

Related U.S. Application Data

(62) Division of application No. 12/571,470, filed on Oct. 1, 2009, now Pat. No. 8,237,020, which is a division of application No. 11/755,248, filed on May 30, 2007, now Pat. No. 7,615,686, which is a division of application No. 10/473,687, filed as application No. PCT/US02/10264 on Apr. 1, 2002, now Pat. No. 7,244,820.

(60) Provisional application No. 60/280,025, filed on Mar. 30, 2001, provisional application No. 60/336,657, filed on Dec. 4, 2001.

(51) Int. Cl.
*C07K 14/325* (2006.01)
*A01N 37/18* (2006.01)

(52) U.S. Cl.
USPC .......................................................... 514/4.5

(58) Field of Classification Search
None
See application file for complete search history.

(56) References Cited

U.S. PATENT DOCUMENTS

| 5,877,012 | A | 3/1999 | Estruch et al. | |
|---|---|---|---|---|
| 6,107,279 | A | 8/2000 | Estruch et al. | |
| 6,137,033 | A | 10/2000 | Estruch et al. | |
| 6,291,156 | B1 | 9/2001 | Estruch et al. | |
| 7,244,820 | B2 * | 7/2007 | Miles et al. | 530/350 |
| 7,615,686 | B2 * | 11/2009 | Miles et al. | 800/302 |
| 8,237,020 | B2 * | 8/2012 | Miles et al. | 800/302 |

FOREIGN PATENT DOCUMENTS

| WO | WO9800546 A2 | 1/1998 |
|---|---|---|
| WO | WO9818932 A2 | 5/1998 |
| WO | WO9833991 A1 | 8/1998 |
| WO | WO9957282 A2 | 11/1999 |
| WO | WO02078437 A2 | 10/2002 |

OTHER PUBLICATIONS

Estruch, et al. 1996, Proceedings National Academy of Science, Vip3, a novel *Bacillus thuringiensis* vegetative insecticidal protein with a wide spectrum of activities against lepidopteran insects, 93: 5389-5394.

Selvapandiyan, A. et al., 1997, Applied and Environmental Microbiology, The *Bacillus thuringiensis* Vegetative Insecticidal Protein Vip3 A Lyses Midgut Epithelium Cells of Susceptible Insects, 67 (12), 5855-5858 (2001).

Yu, et al., 1997, Applied and Environmental Microbiology, Toxicity Analysis of N- and C-Terminus Deleted Vegetative Insecticidal Protein from *Bacillus thuringiensis*, 63: 532-536.

* cited by examiner

*Primary Examiner* — Anne Kubelik
(74) *Attorney, Agent, or Firm* — Karen Magri

(57) ABSTRACT

A novel pesticidal toxin that is highly active against a wide range of lepidopteran insect pests is disclosed. The DNA encoding the pesticidal toxin can be used to transform various prokaryotic and eukaryotic organisms to express the pesticidal toxin. These recombinant organisms can be used to control lepidopteran insects in various environments.

8 Claims, No Drawings

US 8,598,117 B2

PESTICIDAL TOXINS

This application is a Division of co-pending U.S. patent application Ser. No. 12/571,470, filed Oct. 1, 2009, which is a Division of U.S. patent application Ser. No. 11/755,248, filed May 30, 2007, now U.S. Pat. No. 7,615,686, which is a Division of U.S. patent application Ser. No. 10/473,687, filed Sep. 27, 2003, now U.S. Pat. No. 7,244,820, which is a National Stage Entry of PCT/US02/10264, filed Apr. 1, 2002, which claims priority from U.S. Provisional Application No. 60/336,657, filed Dec. 4, 2001 and U.S. Provisional Application No. 60/280,025, filed Mar. 30, 2001, all of which are incorporated herein by reference in their entirety.

FIELD OF THE INVENTION

The present invention relates to novel Vip3 toxins from *Bacillus thuringiensis*, nucleic acid sequences whose expression results in said toxins, and methods of making and methods of using the toxins and corresponding nucleic acid sequences to control insects.

BACKGROUND

Plant pests are a major factor in the loss of the world's important agricultural crops. About $8 billion are lost every year in the U.S. alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts have been shown to provide another tool for the control of economically important insect pests. In particular, the expression of insecticidal toxins in transgenic plants, such as *Bacillus thuringiensis* δ-endotoxins, has provided efficient protection against selected insect pests, and transgenic plants expressing such toxins have been commercialized, allowing farmers to reduce applications of chemical insect control agents.

Other, non-endotoxin genes and the proteins they encode have now been identified. U.S. Pat. Nos. 5,877,012, 6,107,279, 6,137,033, and 6,291,156, as well as Estruch et al. (1996, Proc. Natl. Acad. Sci. 93:5389-5394) and Yu et al. (1997, Appl. Environ. Microbiol. 63:532-536), all herein incorporated by reference, describe a new class of insecticidal proteins called Vip3. Vip3 coding sequences encode approximately 88 kDa proteins that are produced and secreted by *Bacillus* during its vegetative stages of growth (vegetative insecticidal proteins, VIP). The Vip3A protein possesses insecticidal activity against a wide spectrum of lepidopteran pests, including, but not limited to, black cutworm (BCW, *Agrotis ipsilon*), fall armyworm (FAW, *Spodoptera frugiperda*), tobacco budworm (TBW, *Heliothis virescens*), and corn earworm (CEW, *Helicoverpa zea*). More recently, plants expressing the Vip3A protein have been found to be resistant to feeding damage caused by hemipteran insect pests. Thus, the Vip3A protein displays a unique spectrum of insecticidal activities. Other disclosures, WO 98/18932, WO 98/33991, WO 98/00546, and WO 99/57282, have also now identified homologues of the Vip3 class of proteins.

The continued use of chemical and biological control methods heightens the chance for insects to develop resistance to such control measures. Also, only a few specific insect pests are controllable with current measures.

Therefore, there remains a need to discover new and effective pest control agents that provide an economic benefit to farmers and that are environmentally acceptable. Particularly needed are control agents that are targeted to a wider spectrum of economically important insect pests and that efficiently control insect strains that are or could become resistant to existing insect control agents. Furthermore, agents whose application minimizes the burden on the environment are desirable.

SUMMARY

The present invention addresses the need for novel pest control agents by providing new genes and toxins that are distinct from those disclosed in U.S. Pat. Nos. 5,877,012, 6,107,279, and 6,137,033, and Estruch et al. (1996), and Yu et al. (1997), as well as WO 98/18932, WO 99/33991, WO 99/5782, and WO 98/00546.

Within the present invention, compositions and methods for controlling plant pests are provided. In particular, novel vip3 nucleic acid sequences isolated from *Bacillus thuringiensis*, and sequences substantially identical thereto, whose expression results in pesticidal toxins with high specific toxicity to economically important insect pests, particularly insect pests that infest plants, are provided. The invention is further drawn to the novel pesticidal toxins resulting from the expression of the nucleic acid sequences, and to compositions and formulations containing the pesticidal toxins, which are capable of inhibiting the ability of insect pests to survive, grow and reproduce, or of limiting insect-related damage or loss to crop plants. The invention is also drawn to methods of using the nucleic acid sequences, for example in making hybrid toxins with enhanced pesticidal activity or in a recombinogenic procedure such as DNA shuffling. The invention is further drawn to a method of making the toxins and to methods of using the nucleic acid sequences, for example in microorganisms to control insects or in transgenic plants to confer protection from insect damage, and to a method of using the pesticidal toxins, and compositions and formulations comprising the pesticidal toxins, for example applying the pesticidal toxins or compositions or formulations to insect-infested areas, or to prophylactically treat insect-susceptible areas or plants to confer protection against the insect pests.

The novel pesticidal toxins described herein are highly active against insects. For example, a number of economically important insect pests, such as the lepidopterans *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Diatraea grandiosella* (southwestern corn borer), *Diatraea saccharalis* (sugarcane borer), *Sesamia nonagroides* (mediterranean corn borer), *Helicoverpa punctigera* (native budworm) and *Helicoverpa armigera* (cotton bollworm) can be controlled by the pesticidal toxins. The pesticidal toxins can be used singly or in combination with other insect control strategies to confer maximal pest control efficiency with minimal environmental impact.

According to one aspect, the present invention provides an isolated nucleic acid molecule comprising a nucleotide sequence that encodes a toxin that is active against insects, wherein the nucleotide sequence: (a) has at least 92% sequence identity with SEQ ID NO: 1; or (b) is isocoding with the nucleotide sequence of (a); or (c) encodes an amino acid sequence that has at least 91% sequence identity with SEQ ID NO: 3.

In one embodiment of this aspect, the isolated nucleic acid molecule comprises a nucleotide sequence that has at least 92% sequence identity with SEQ ID NO: 1.

In another embodiment of this aspect, the isolated nucleic acid molecule comprises a nucleotide sequence that is isocoding with a nucleotide sequence that has at least 92% sequence identity with SEQ ID NO: 1.

In a further embodiment, the isolated nucleic acid molecule comprises the nucleotide sequence set forth in SEQ ID NO: 1 or SEQ ID NO: 3.

In another embodiment of this aspect, the isolated nucleic acid molecule comprises a nucleotide sequence that encodes an amino acid sequence with at least 91% sequence identity with SEQ ID NO: 2. In a further embodiment, the isolated nucleic acid molecule comprises a nucleotide sequence that encodes the amino acid sequence set forth in SEQ ID NO: 3.

In one embodiment, the isolated nucleic acid molecule comprises the approximately 2.4 kb DNA fragment comprised in pNOV1325 harbored in *E. coli* strain DH5α, designated as ATCC PTA-3868. In another embodiment, the isolated nucleic acid molecule comprises the approximately 2.4 kb DNA fragment comprised in pNOV1328 harbored in *E. coli* DH5α, designated as ATCC PTA-3869.

According to one embodiment of the invention, the isolated nucleic acid molecule encodes a toxin that is active against a lepidopteran insect. In a further embodiment, the lepidopteran insect is selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth).

The present invention also provides a chimeric gene comprising a heterologous promoter sequence operatively linked to the nucleic acid molecule of the invention. Further, the present invention provides a recombinant vector comprising such a chimeric gene. The present invention also provides a virus comprising such a chimeric gene. A virus according to this aspect of the invention may be an animal virus or a plant virus. Still further, the present invention provides a transgenic host cell comprising such a chimeric gene. A transgenic host cell according to this aspect of the invention may be an animal cell, a bacterial cell, a yeast cell or a plant cell, preferably, a plant cell. Even further, the present invention provides a transgenic plant comprising such a plant cell. A transgenic plant according to this aspect of the invention may be sorghum, wheat, sunflower, tomato, cole crops, cotton, rice, soybean, sugar beet, sugarcane, tobacco, barley, oilseed rape or maize, preferably maize. Still further, the present invention provides seed from the group of transgenic plants consisting of sorghum, wheat, sunflower, tomato, cole crops, cotton, rice, soybean, sugar beet, sugarcane, tobacco, barley, oilseed rape and maize. In a further embodiment, the seed is from a transgenic maize plant.

Also provided by the present invention are transgenic plants further comprising a second nucleic acid sequence or groups of nucleic acid sequences that encode a second pesticidal principle. Particularly preferred second nucleic acid sequences are those that encode a δ-endotoxin, those that encode another Vegetative Insecticidal Protein toxin or those that encode a pathway for the production of a non-proteinaceous pesticidal principle.

According to one aspect, the present invention provides an isolated toxin that is active against insects, wherein the toxin comprises an amino acid sequence that: (a) has at least 91% sequence identity with SEQ ID NO: 2; or (b) is produced by the expression of a nucleic acid molecule comprising a nucleotide sequence that has at least 92% sequence identity with SEQ ID NO: 1.

In one embodiment of this aspect, the isolated toxin comprises an amino acid sequence that has at least 91% sequence identity with SEQ ID NO: 2.

In a further embodiment, the isolated toxin comprises the amino acid sequence set forth in SEQ ID NO: 2.

In another embodiment of this aspect, the isolated toxin is produced by the expression of a nucleic acid molecule comprising a nucleotide sequence that has at least 92% sequence identity with SEQ ID NO: 1.

In yet another embodiment, the isolated toxin is produced by the expression of a nucleic acid molecule comprising the nucleotide sequence set forth in SEQ ID NO: 1 or SEQ ID NO: 3.

In another embodiment, the toxins of the invention are active against lepidopteran insects. In a further embodiment, the toxins are active against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth).

In a further embodiment, the toxins are produced by the *E. coli* strain deposited as ATCC accession PTA-3868 or the *E. coli* strain deposited as ATCC accession PTA-3869.

The present invention also provides a composition comprising an effective insect-controlling amount of a toxin according to the invention.

In another aspect, the present invention provides a method of producing a toxin that is active against insects, comprising: (a) obtaining a transgenic host cell comprising a chimeric gene, which itself comprises a heterologous promoter sequence operatively linked to the nucleic acid molecule of the invention; and (b) expressing the nucleic acid molecule in the transgenic cell, which results in at least one toxin that is active against insects.

In a further aspect, the present invention provides a method of producing an insect-resistant transgenic plant, comprising introducing a nucleic acid molecule of the invention into the transgenic plant, wherein the nucleic acid molecule is expressible in the transgenic plant in an effective amount to control insects. According to one embodiment, the insects are lepidopteran insects. In a further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth).

In a still further aspect, the present invention provides a method of controlling insects comprising delivering to the insects an effective amount of a toxin of the present invention. According to one embodiment, the insects are lepidopteran insects. In a further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth). In another embodiment, the toxin is delivered to the insects orally. In a still further embodiment, the toxin is delivered orally through a transgenic plant comprising a nucleic acid sequence that expresses a toxin of the present invention.

The present invention also provides hybrid toxins active against insects, wherein the hybrid toxins are encoded by a nucleic acid molecule comprising a nucleotide sequence according to the invention.

In one embodiment, the hybrid toxins of the invention are active against lepidopteran insects. In a further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth)

In another embodiment, the hybrid toxin is encoded by the nucleotide sequence set forth in SEQ ID NO: 6.

The present invention also provides a composition comprising an insecticidally effective amount of a hybrid toxin according to the invention.

In another aspect, the present invention provides a method of producing a hybrid toxin active against insects, comprising: (a) obtaining a transgenic host cell comprising a chimeric gene, which itself comprises a heterologous promoter sequence operatively linked to the nucleic acid molecule of the invention; and (b) expressing the nucleic acid molecule in the transgenic cell, which results in at least one hybrid toxin that is active against insects.

In a further aspect, the present invention provides a method of producing an insect-resistant transgenic plant, comprising introducing a nucleic acid molecule of the invention into the plant, wherein the nucleic acid molecule encodes a hybrid toxin and wherein the hybrid toxin is expressible in the transgenic plant in an effective amount to control an insect. According to one embodiment, the insects are lepidopteran insects. In another embodiment, the lepidopteran insect is selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

In a still further aspect, the present invention provides a method of controlling an insect comprising delivering to the insects an effective amount of a hybrid toxin of the present invention. According to one embodiment, the insects are lepidopteran insects. In a further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth). In another embodiment, the hybrid toxin is delivered to the insects orally. In a further embodiment, the hybrid toxin is delivered orally through a transgenic plant comprising a nucleic acid sequence that expresses a hybrid toxin of the present invention.

The present invention also provides a hybrid toxin active against insects, comprising a carboxy-terminal region of a Vip3 toxin joined in the amino to carboxy direction to an amino-terminal region of a different Vip3 toxin, wherein the carboxy-terminal region comprises an amino acid sequence which has at least 75% identity with amino acids 579-787 of SEQ ID NO: 2; and wherein the amino-terminal region has at least 75% identity with amino acids 1-578 of SEQ ID NO: 4. In a further embodiment, the carboxy-terminal region comprises amino acids 578-787 of SEQ ID NO: 2, and the amino-terminal region comprises amino acids 1-579 of SEQ ID NO: 5. In a still further embodiment, the hybrid toxin comprises amino acids 1-787 of SEQ ID NO: 7.

The hybrid toxin, according to this aspect of the invention, is active against lepidopteran insects. In a further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

Also encompassed by this aspect of the invention is a nucleic acid molecule comprising a nucleotide sequence that encodes the hybrid toxin of this aspect.

Also provided by the invention is a method of controlling insects wherein the transgenic plant further comprises a second nucleic acid sequence or groups of nucleic acid sequences that encode a second pesticidal principle. Particularly preferred second nucleic acid sequences are those that encode a δ-endotoxin, those that encode another Vegetative Insecticidal Protein toxin or those that encode a pathway for the production of a non-proteinaceous pesticidal principle.

Yet another aspect of the present invention is the provision of a method for mutagenizing a nucleic acid molecule according to the present invention, wherein the nucleic acid molecule has been cleaved into populations of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with polymerase under conditions which result in the annealing of the single-stranded fragments at the areas of identity to form pairs of annealed fragments, the areas of identity being sufficient for one member of the pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO: 1 is the coding sequence of the native vip3B gene.
SEQ ID NO: 2 is the amino acid sequence encoded SEQ ID NO: 1.
SEQ ID NO: 3 is the coding sequence of the maize optimized vip3B gene.
SEQ ID NO: 4 is the coding sequence of the native vip3A gene.
SEQ ID NO: 5 is the amino acid sequence encoded by SEQ ID NO: 4.
SEQ ID NO: 6 is the coding sequence of the hybrid vip3A-B gene.
SEQ ID NO: 7 is the amino acid sequence encoded by SEQ ID NO: 6.
SEQ ID NO: 8-13 are primers useful in the present invention.

Deposits

The following material was deposited with the American Type Culture Collection, 10801 University Blvd., Manassas, Va., under the terms of the Budapest Treaty on the International Recognition of the Deposit of Microorganisms for the Purposes of Patent Procedure. All restrictions on the availability of the deposited material will be irrevocably removed upon granting of the patent.

| Clone | Accession Number | Date of Deposit |
| --- | --- | --- |
| pNOV1325 | ATCC No. PTA-3868 | Nov. 16, 2001 |
| pNOV1328 | ATCC No. PTA-3869 | Nov. 16, 2001 |

Definitions

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Effective insect-controlling amount" means that concentration of toxin that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion.

A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Hybrid toxin" as used herein is an insecticidal toxin made by the hand of man which comprises amino acid regions or fragments of one toxin joined with amino acid regions or fragments from a different toxin, For example, without limitation, joining the C-terminal region of Vip3B, from amino acid number 579 to amino acid number 787 of SEQ ID NO: 2, with the N-terminal region of Vip3A, from amino acid number 1 to amino acid number 578 of SEQ ID NO: 5.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase 11 and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

A "shuffled" nucleic acid is a nucleic acid produced by a shuffling procedure such as any shuffling procedure set forth herein. Shuffled nucleic acids are produced by recombining (physically or virtually) two or more nucleic acids (or character strings), e.g., in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

Substantially identical: the phrase "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith &

Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2× SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1× SSC at 45° C. for 15 minutes. An example low stringency wash for a duplex of, e.g., more than 100 nucleotides, is 4-6× SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2× SSC, 0.1% SDS at 50° C., more desirably in 7% sodium dodecyl sulfate (SDS), 0.5 M $NaPO_4$, 1 mM EDTA at 50° C. with washing in 1× SSC, 0.1% SDS at 50° C., more desirably still in 7% sodium dodecyl sulfate (SDS), 0.5 M $NaPO_4$, 1 mM EDTA at 50° C. with washing in 0.5× SSC, 0.1% SDS at 50° C., preferably in 7% sodium dodecyl sulfate (SDS), 0.5 M $NaPO_4$, 1 mM EDTA at 50° C. with washing in 0.1× SSC, 0.1% SDS at 50° C., more preferably in 7% sodium dodecyl sulfate (SDS), 0.5 M NaPO₄, 1 mM EDTA at 50° C. with washing in 0.1× SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The "Vip3 class of proteins" comprises, for example, without limitation, Vip3A(a), Vip3A(b), Vip3A(c), Vip3B, Vip3C(a), Vip3C(b), Vip3Z, and their homologues. "Homologue" is used herein to mean that the indicated protein or polypeptide bears a defined relationship to other members of the Vip3 class of proteins. This defined relationship includes but is not limited to, 1) proteins which are at least 70%, more preferably at least 80% and most preferably at least 90% identical at the sequence level to another member of the Vip3 class of proteins while also retaining pesticidal activity, 2) proteins which are cross-reactive to antibodies which immunologically recognize another member of the Vip3 class of proteins, 3) proteins which are cross-reactive with a receptor to another member of the Vip3 class of proteins and retain the ability to induce programmed cell death, and 4) proteins which are at least 70%, more preferably at least 80% and most preferably at least 90% identical at the sequence level to the toxic core region of another member of the Vip3 class of proteins while also retaining pesticidal activity. Other Vip3 homologues have been disclosed in WO 98/18932, WO 98/33991, WO 98/00546, and WO 99/57282

Nucleotides are indicated by their bases by the following standard abbreviations: adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION

This invention relates to nucleic acid sequences whose expression results in novel toxins, and to the making and using of the toxins to control insect pests. The nucleic acid sequences are derived from *Bacillus*, a gram-positive spore-forming microorganism. In particular, novel Vip3 proteins, useful as pesticidal agents, are provided.

For purposes of the present invention, insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Lepidoptera.

The expression of the nucleic acid sequences of the present invention results in toxins that can be used to control lepidopteran insects such as *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth).

In one embodiment, the invention encompasses an isolated nucleic acid molecule comprising a nucleotide sequence that has at least 92% sequence identity with SEQ ID NO: 1, wherein expression of the isolated nucleic acid molecule results in insect control activity. When expressed in a heterologous host, the nucleic acid molecule of SEQ ID NO: 1 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth), showing that the nucleotide sequence set forth in SEQ ID NO: 1 is sufficient for such insect control activity. In a further embodiment, the isolated nucleic acid molecule comprises a nucleotide sequence that has at least 93% sequence identity with SEQ ID NO: 1. In a still further embodiment, the isolated nucleic acid molecule comprises a nucleotide sequence that has at least 94% sequence identity with SEQ ID NO: 1. In a still further embodiment, the isolated nucleic acid molecule comprises a nucleotide sequence that has at least 95% sequence identity with SEQ ID NO: 1. In a still further embodiment, the isolated nucleic acid molecule comprises a nucleotide sequence that has at least 96% sequence identity with SEQ ID NO: 1. In a still further embodiment, the isolated nucleic acid molecule comprises a nucleotide sequence that has at least 97% sequence identity with SEQ ID NO: 1. In a still further embodiment, the isolated nucleic acid molecule comprises a nucleotide sequence that has at least 98% sequence identity with SEQ ID NO: 1. In a still further embodiment, the isolated nucleic acid molecule comprises a nucleotide sequence that has at least 99% sequence identity with SEQ ID NO: 1. In a still further embodiment, the isolated nucleic acid molecule comprises the nucleotide sequence set forth in SEQ ID NO: 1.

In another embodiment, the invention encompasses a nucleic acid molecule comprised in pNOV 1325, whose expression results in an insecticidal toxin, which is deposited in the *E. coli* strain DH5α designated ATCC accession number PTA-3868.

In one embodiment, the invention encompasses an isolated nucleic acid molecule comprising a nucleotide sequence that is isocoding with a nucleotide sequence that has at least 92% sequence identity with SEQ ID NO: 1, wherein expression of the isolated nucleic acid molecule results in insect control activity. When expressed in a heterologous host, the nucleic acid molecule of SEQ ID NO: 3 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm) and *Helicoverpa armigera* (cotton bollworm), showing that the nucleotide sequence set forth in SEQ ID NO: 3 is sufficient for such insect control activity. In a further embodiment, the invention encompasses a nucleic acid molecule comprised in pNOV 1328, whose expression results in an insecticidal toxin, which is deposited in the *E. coli* strain DH5α designated ATCC accession number PTA-3869.

In another embodiment, the isolated nucleic acid molecule encodes a toxin comprising an amino acid sequence which has at least 91% sequence identity to the amino acid sequence set forth in SEQ ID NO: 2. In a further embodiment, the isolated nucleic acid molecule encodes a toxin comprising an amino acid sequence which has at least 92% sequence identity to the amino acid sequence set forth in SEQ ID NO: 2. In a still further embodiment, the isolated nucleic acid molecule encodes a toxin comprising an amino acid sequence which has at least 93% sequence identity to the amino acid sequence set forth in SEQ ID NO: 2. In a still further embodiment, the isolated nucleic acid molecule encodes a toxin comprising an amino acid sequence which has at least 94% sequence identity to the amino acid sequence set forth in SEQ ID NO: 2. In a still further embodiment, the isolated nucleic acid molecule encodes a toxin comprising an amino acid sequence which has at least 95% sequence identity to the amino acid sequence set forth in SEQ ID NO: 2. In a still further embodiment, the isolated nucleic acid molecule encodes a toxin comprising an amino acid sequence which has at least 96% sequence identity to the amino acid sequence set forth in SEQ ID NO: 2. In a still further embodiment, the isolated nucleic acid molecule encodes a toxin comprising an amino acid sequence which has at least 97% sequence identity to the amino acid sequence set forth in SEQ ID NO: 2. In a still further embodiment, the isolated nucleic acid molecule encodes a toxin comprising an amino acid sequence which has at least 98% sequence identity to the amino acid sequence set forth in SEQ ID NO: 2. In a still further embodiment, the isolated nucleic acid molecule encodes a toxin comprising an amino acid sequence which has at least 99% sequence identity to the amino acid sequence set forth in SEQ ID NO: 2. In a still further embodiment, the isolated nucleic acid molecule encodes a toxin comprising the amino acid sequence set forth in SEQ ID NO: 2.

The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E. coli* or *Bacillus*. In another embodiment, host cells for such recombinant vectors are endophytes or epiphytes. A preferred host cell for such vectors is a eukaryotic cell, such as a yeast cell, a plant cell, or an insect cell. Plant cells such as maize cells are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of such host cells. In one, such host cells are prokaryotic cells. In a preferred embodiment, such host cells are eukaryotic cells, such as yeast cells, insect cells, or plant cells. In a most preferred embodiment, the host cells are plant cells, such as maize cells.

The present invention also provides a method of producing a toxin that is active against insects, comprising (a) obtaining a transgenic host cell according to the invention and (b) expressing a nucleic acid molecule of the invention in the transgenic host cell which results in at least one toxin that is active against insects.

The present invention further provides a method of producing an insect-resistant transgenic plant, comprising introducing a nucleic acid molecule of the invention into the transgenic plant, wherein the nucleic acid molecule is expressible in the transgenic plant in an effective amount to control insects. In a still further embodiment the insects are lepidopteran insects. In a still further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth).

In another aspect, the present invention provides an isolated toxin that is active against insects, wherein the toxin comprises an amino acid sequence that: (a) has at least 91% sequence identity with SEQ ID NO: 2; or (b) is encoded by a nucleic acid molecule comprising a nucleotide sequence that has at least 92% sequence identity with SEQ ID NO: 1.

In one embodiment, the present invention provides an isolated toxin that is active against insects, wherein the toxin comprises an amino acid sequence that has at least 91% sequence identity with SEQ ID NO: 2. In a further embodiment, the toxin comprises an amino acid sequence that has at least 92% sequence identity with SEQ ID NO: 2. In a still further embodiment, the toxin has at least 93% sequence identity with SEQ ID NO: 2. In a still further embodiment, the toxin has at least 94% sequence identity with SEQ ID NO: 2. In a still further embodiment, the toxin has at least 95% sequence identity with SEQ ID NO: 2. In a still further embodiment, the toxin has at least 96% sequence identity with SEQ ID NO: 2. In a still further embodiment, the toxin has at least 97% sequence identity with SEQ ID NO: 2. In a still further embodiment, the toxin has at least 98% sequence identity with SEQ ID NO: 2. In a still further embodiment, the toxin has at least 99% sequence identity with SEQ ID NO: 2. In a still further embodiment, the toxin comprises the amino acid sequence set forth in SEQ ID NO: 2.

In one embodiment, the present invention provides a toxin active against insects, wherein the toxin is produced by the expression of a nucleic acid molecule comprising a nucleotide sequence that has at least 92% sequence identity with SEQ ID NO: 1. In a further embodiment, the nucleotide sequence has at least 93% sequence identity with SEQ ID NO: 1. In a still further embodiment, the nucleotide sequence has at least 94% sequence identity with SEQ ID NO: 1. In a still further embodiment, the nucleotide sequence has at least 95% sequence identity with SEQ ID NO: 1. In a still further embodiment, the nucleotide sequence has at least 96% sequence identity with SEQ ID NO: 1. In a still further embodiment, the nucleotide sequence has at least 97% sequence identity with SEQ ID NO: 1. In a still further embodiment, the nucleotide sequence has at least 98% sequence identity with SEQ ID NO: 1. In a still further embodiment, the nucleotide sequence has at least 99% sequence identity with SEQ ID NO: 1. In a still further embodiment, the toxin is produced by the expression of a nucleotide sequence comprising nucleotides 1-2364 of SEQ ID NO: 1 or nucleotides 1-2364 of SEQ ID NO: 3.

In one embodiment, a toxin of the present invention is produced by the expression of a nucleotide sequence comprising the approximately 2.4 kb DNA fragment comprised in pNOV1325, deposited as ATCC accession number PTA-3868. In another embodiment, a toxin of the present invention is produced by the expression of a nucleotide sequence comprising the approximately 2.4 kb DNA fragment comprised in pNOV1328, deposited as ATCC accession number PTA-3869.

In another embodiment, a toxin of the present invention is produced by the *E. coli* strain designated as ATCC accession PTA-3868. In still another embodiment, the toxin is produced by the *E. coli* strain designated as ATCC accession PTA-3869.

The toxins of the present invention have insect control activity when tested against insect pests in bioassays. In one embodiment, the toxins of the invention are active against lepidopteran insects. In a further embodiment, the lepidopteran insects are selected from the group consisting of *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Helicoverpa punctigera* (native budworm), *Helicoverpa armigera* (cotton bollworm), *Manduca sexta* (tobacco hornworm), *Trichoplusia ni* (cabbage looper), *Pectinophora gossypiella* (pink bollworm), and *Cochylis hospes* (banded sunflower moth). The insect controlling properties of the insecticidal toxins of the invention are further illustrated in Example 5 and Example 8.

The present invention also encompasses hybrid toxins which are active against insects, wherein the hybrid toxins are encoded by nucleic acid molecules comprising a nucleotide sequence that: (a) has a compliment that hybridizes to nucleotides 1734-2364 of SEQ ID NO: 1 in 7% sodium dodecyl sulfate (SDS), 0.5 M NaPO$_4$, 1 mM EDTA at 50° C. with washing in 0.1× SSC, 0.1% SDS at 65° C.; or (b) is isocoding with the nucleotide sequence of (a); or (c) comprises a consecutive 20 base pair nucleotide portion identical in sequence to a consecutive 20 base pair nucleotide portion of a nucleotide sequence of (a) or (b), wherein expression of the nucleic acid molecule results in insect control activity. Specifically exemplified herein is a hybrid toxin that is encoded by the nucleotide sequence set forth in SEQ ID NO: 6. When expressed in a heterologous host, the nucleic acid molecule of SEQ ID NO: 6 results in insect control activity against *Ostrinia nubilalis* (European corn borer), *Plutella xylostella* (diamondback moth), *Spodoptera frugiperda* (fall armyworm), *Agrotis ipsilon* (black cutworm), *Helicoverpa zea* (corn earworm), *Heliothis virescens* (tobacco budworm), *Spodoptera exigua* (beet armyworm), *Pectinophora gossypiella* (pink boll worm), *Trichoplusia ni* (cabbage looper), *Cochyles hospes* (banded sunflower moth), and *Homoeosoma electellum* (sunflower head moth).

The present invention also encompasses hybrid toxins active against insects that comprise a carboxy-terminal region of a Vip3 toxin joined in the amino to carboxy direction to an amino-terminal region of a different Vip3 toxin, wherein the carboxy-terminal region comprises an amino acid sequence which has at least 75% identity with amino acids 579-787 of SEQ ID NO: 2; and wherein the amino-terminal region has at least 75% identity with amino acids 1-578 of SEQ ID NO: 5. In a further embodiment, the carboxy-terminal region comprises amino acids 579-787 of SEQ ID NO: 2, and the amino-terminal region comprises amino acids 1-578 of SEQ ID NO: 5. In a still further embodiment, the hybrid toxin comprises amino acids 1-787 of SEQ ID NO: 6.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, *B. thuringiensis* cells comprising modifications of a nucleotide sequence of this invention are made. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to *Bacillus thuringiensis* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In:Industrial Microorganisms:Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In:Industrial microorganisms:basic and applied molecular genetics, Baltz, Hegeman, and Skatrud eds., American Society for Microbiology, Washington (1993); Dequin & Bane, Biotechnology L2:173-177 (1994); van den Berg et al., Biotechnology 8:135-139 (1990)).

Plant Transformation

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962, EP 0 359 4721, and WO 93/07278.

In one embodiment of the invention the vip3B gene is made according to the procedure disclosed in U.S. Pat. No. 5,625,136, herein incorporated by reference. In this procedure, maize preferred codons, i.e., the single codon which most frequently encodes that amino acid in maize, are used. The maize preferred codon for a particular amino acid may be derived, for example, from known gene sequences from maize. Maize codon usage for 28 genes from maize plants is found in Murray et al., Nucleic Acids Research 17:477-498 (1989), the disclosure of which is incorporated herein by reference. A synthetic sequence made with maize optimized codons is set forth in SEQ ID NO: 2.

In this manner, the nucleotide sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

The novel vip3 toxin genes of the present invention, either as their native sequence or as optimized synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable.

Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred constitutive promoters include the CaMV 35S and 19S promoters (Fraley et al., U.S. Pat. No. 5,352,605 issued Oct. 4, 1994). An additionally preferred promoter is derived from any one of several of the actin genes, which are expressed in most cell types. The promoter expression cassettes described by McElroy et al. (Mol. Gen. Genet. 231: 150-160 (1991)) can be easily modified for the expression of the novel toxin gene and are particularly suitable for use in monocotyledonous hosts.

Yet another preferred constitutive promoter is derived from ubiquitin, which is another gene product known to accumulate in many cell types. A ubiquitin promoter has been cloned from several species for use in transgenic plants, for example, sunflower (Binet et al., 1991. Plant Science 79: 87-94), maize (Christensen et al., 1989. Plant Molec. Biol. 12: 619-632), and arabidopsis (Norris et al. 1993. Plant Molec. Biol. 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin genes of the invention in plants, particularly maize, are those that direct expression in root, pith, leaf or pollen. Such promoters are disclosed in WO 93/07278, herein incorporated by reference in its entirety. Other tissue specific promoters useful in the present invention include the cotton rubisco promoter disclosed in U.S. Pat. No. 6,040,504; the rice sucrose synthase promoter disclosed in U.S. Pat. No. 5,604,121; and the cestrum yellow leaf curling virus promoter disclosed in WO 01/73087, all incorporated by reference. Chemically inducible promoters useful for directing the expression of the novel toxin gene in plants are disclosed in U.S. Pat. No. 5,614,395 herein incorporated by reference in its entirety.

The nucleotide sequences of this invention can also be expressed under the regulation of promoters that are chemically regulated. This enables the Vip3 toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells that need to synthesize the insecticidal toxins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Preferred tissue specific expression patterns include green tissue specific, root specific, stem specific, and flower specific. Promoters suitable for expression in green tissue include many that regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12:579-589 (1989)). A preferred promoter for root specific expression is that described by de Framond (FEBS 290:103-106 (1991); EP 0 452 269 to Ciba-Geigy). A preferred stem specific promoter is that described in U.S. Pat. No. 5,625,136 (to Ciba-Geigy) and which drives expression of the maize trpA gene.

Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). The choice of selectable marker is not, however, critical to the invention.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et aL (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransf erase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

Combinations of Insect Control Principles

The pesticidal toxins of the invention can be used in combination with Bt δ-endotoxins or other pesticidal principles to increase pest target range. Furthermore, the use of the pesticidal toxins of the invention in combination with Bt δ-endotoxins or other pesticidal principles of a distinct nature has particular utility for the prevention and/or management of insect resistance.

The various insecticidal crystal proteins from *Bacillus thuringiensis* have been classified based upon their spectrum of activity and sequence similarity. The classification put forth by Hofte and Whiteley, Microbiol. Rev. 53: 242-255 (1989) placed the then known insecticidal crystal proteins into four major classes. Generally, the major classes are defined by the spectrum of activity, with the Cry1 proteins active against Lepidoptera, Cry2 proteins active against both Lepidoptera and Diptera, Cry3 proteins active against Coleoptera, and Cry4 proteins active against Diptera.

Within each major class, the δ-endotoxins are grouped according to sequence similarity. The Cry1 proteins are typically produced as 130-140 kDa protoxin proteins that are proteolytically cleaved to produce active toxins that are about 60-70 kDa. The active portion of the δ-endotoxin resides in the $NH_2$-terminal portion of the full-length molecule. Hofte and Whiteley, supra, classified the then known Cry1 proteins into six groups, 1Aa, 1Ab, 1Ac, 1B, 1C, and 1D. Since then, proteins classified as Cry1Ea, Cry1Fa, Cry9A, Cry9C and Cry9B, as well as others, have also been characterized.

The spectrum of insecticidal activity of an individual δ-endotoxin from *Bacillus thuringiensis* tends to be quite narrow, with a given δ-endotoxin being active against only a few insects. Specificity is the result of the efficiency of the various steps involved in producing an active toxin protein and its subsequent ability to interact with the epithelial cells in the insect digestive tract. In one preferred embodiment, expression of the nucleic acid molecules of the invention in transgenic plants is accompanied by the expression of one or more Bt δ-endotoxins. Particularly preferred Bt δ-endotoxins are those disclosed in U.S. Pat. No. 5,625,136, herein incorporated by reference.

It is well known that many δ-endotoxin proteins from *Bacillus thuringiensis* are actually expressed as protoxins. These protoxins are solubilized in the alkaline environment of the insect gut and are proteolytically converted by proteases into a toxic core fragment (Hofte and Whiteley, Microbiol. Rev. 53: 242-255 (1989)). For δ-endotoxin proteins of the Cry1 class, the toxic core fragment is localized in the N-terminal half of the protoxin. It is within the scope of the present invention that genes encoding either the full-length protoxin form or the truncated toxic core fragment of the novel toxin proteins can be used in plant transformation vectors to confer insecticidal properties upon the host plant.

Other insecticidal principles include protease inhibitors (both serine and cysteine types), lectins, α-amylase, peroxidase and cholesterol oxidase. Other Vip coding sequences, such as vip1A(a) and vip2A(a) as disclosed in U.S. Pat. No. 5,849,870 and herein incorporated by reference, are also useful in the present invention.

This co-expression of more than one insecticidal principle in the same transgenic plant can be achieved by genetically engineering a plant to contain and express all the genes necessary. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

The present invention further encompasses variants of the disclosed nucleic acid molecules. Naturally occurring variant sequences can be identified and/or isolated with the use of well-known molecular biology techniques, as, for example, with PCR and hybridization techniques as outlined below.

Variant vip3 nucleotide sequences include synthetically derived nucleotide sequences, such as those generated, for example, by using site-directed mutagenesis or those made by whole domain swaps, but which still exhibit pesticidal activity. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Generally, a nucleotide sequence of the invention will have at least 80%, preferably 85%, 90%, 95%, up to 98% or more sequence identity to its respective reference vip3 nucleotide sequence, and have pesticidal activity.

Variant vip3 nucleotide sequences also encompass sequences derived from a mutagenic and recombinogenic procedure such as DNA shuffling. With such a procedure, one or more different vip3 sequences of the present invention, for example, without limitation, vip3B and vip3A-B can be recombined together or with other vip3 or related sequences, for example, and without limitation, vip3A (SEQ ID NO: 5), to create new vip3 nucleic acid molecules encoding Vip3 toxins possessing the desired properties. In this manner, libraries of recombinant vip3 polynucleotides are generated from a population of sequence related vip3 polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; International Patent Application WO 99/57128, and U.S. Pat. Nos. 5,605,793, 5,837,458 and 6,335,179.

Mutagenesis methods as disclosed herein can be combined with high-throughput, screening methods to detect the pesticidal activity of cloned, mutagenized Vip3 polypeptides in host cells. Mutagenized DNA molecules that encode active Vip3 polypeptides (e.g., secreted and detected by antibodies; or insecticidal in an insect bioassay) can be recovered from the host cells and rapidly sequenced using standard art procedures. These methods allow the rapid determination of the importance of individual amino acid residues in a Vip3 polypeptide of interest, and can be applied to polypeptides of unknown structure.

The libraries of recombinant vip3 genes that are produced using DNA shuffling methods are screened to identify those that exhibit improved properties for use in protecting plants against pests. Included among properties for which DNA shuffling is useful for obtaining improved vip3 pest resistance genes are increased potency against a target pest, increased target pest range, decreased susceptibility to development of resistance by pests, increased expression level, increased resistance to protease degradation, increased stability in environmental conditions, and reduced toxicity to a host plant. By using an appropriate screening strategy, one can simultaneously or sequentially obtain vip3 genes that are optimized for more than one property.

DNA shuffling is useful for obtaining vip3 pest resistance genes that encode toxins that exhibit enhanced potency against a target pest. Once the shuffling is completed, the resulting library of shuffled vip3 genes is screened to identify those that exhibit enhanced pesticidal activity. One way of performing this screening is to clone the protein-coding region of the shuffled vip3 genes into an expression vector that is suitable for expressing the genes in a chosen host cell such as, for example, E. coli or a crystal minus strain of Bacillus thuringiensis. One skilled in the art will recognize the advantages and disadvantages of using either of these two expression systems. For example, Bacillus thuringiensis would be more desirable in producing secreted Vip3 proteins. If desired, clones can be subjected to a preliminary screen, for example, by immunoassay, to identify those that produce a Vip3 protein of the correct size. Those that are positive in the preliminary screen are then tested in a functional screen to identify shuffled vip3 genes that encode a toxin having the desired enhanced activity.

A whole insect assay can be used for determining toxicity. In these assays, the Vip3 toxins expressed from the shuffled vip3 genes are placed on insect diet, for example, artificial diet or plant tissue, and consumed by the target insect. Those clones causing growth inhibition or mortality to the target insect can be tested in further bioassays to determine potency. Shuffled vip3 genes encoding toxins with enhanced potency can be identified as those that have a decreased $EC_{50}$ (concentration of toxin necessary to reduce insect growth by 50%) and/or $LC_{50}$ (concentration of toxin necessary to cause 50% mortality).

In vitro assays can also be used for screening shuffled vip3 gene libraries. Such assays typically involve the use of cultured insect cells that are susceptible to Vip3 toxins, and/or cells that express a receptor for the Vip3 toxins, either naturally or as a result of expression of a heterologous gene. Other in vitro assays can be used, for example, detection of morphological changes in cells, dyes and labels useful for detecting cell death, or detection of the release of ATPase by cells. One example of a suitable in vitro assay using cultured insect cells for Vip3 toxicity is Sf9 (Spodoptera frugiperda) cells. Sf9 is highly sensitive to Vip3 toxins. When Vip3 toxins are mixed with Sf9 cells, the cell membrane becomes highly permeable to small molecules. When a dye such as trypan blue is added to the cell suspension, those cells which are killed by the Vip3 toxin are stained blue. Thus, the cytotoxicity of the Vip3 toxin can be determined by image analysis.

Additional in vitro assays involve the use of receptors for the Vip3 toxins. One such receptor is disclosed in U.S. Pat. No. 6,291,156, herein incorporated by reference. The Vip3 receptor protein can be immobilized on a receiving surface, for example, without limitation, a 96-well plate or a nitrocellulose membrane, and exposed to clones comprising shuffled vip3 genes. Thus, shuffled vip3 genes that encode functional toxins can be identified on the basis of binding affinity to the Vip3 receptor. Further, the gene encoding the Vip3 receptor can be transformed into a non-Vip3 susceptible cell line, for example the Schneider 2 (S2) Drosophila cell line, using methods known in the art (see for example, Clem and Miller, 1194, Mol. Cel. Biol. 14:5212-522). The transformed S2 cells can then be exposed to clones comprising shuffled vip3 genes. Thus, shuffled vip3 genes that encode functional toxins can be identified on the basis of induction of cell death.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by Ansubel (ed.) Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, NY (1998); and by T. J. Silhavy, M. L. Berman, and L. W. Enquist, Experiments with Gene Fusions, Cold Spring Harbor Laboratory, Cold Spring Harbor, N.Y. (1984).

Example 1

Construction of Cosmid Library from Bacillus thuringiensis Strain AB1183

Total DNA was isolated from a Bacillus thuringiensis strain, designated AB1183, by treating freshly grown cells resuspended in 100 mM Tris pH 8, 10 mM EDTA with 2 mg/ml lysozyme for 30 minutes at 37° C. Proteinase K was added to a final concentration of 100 µg/ml in 1% SDS, 50 mM EDTA, 1M urea and incubated at 55° C. An equal volume of phenol-chloroform-isoamyl alcohol was added. The sample was gently mixed for 5 minutes and centrifuged at 3K. This was repeated twice. The aqueous phase was then mixed with 0.7 volumes isopropanol and centrifuged. The DNA pellet was washed three times with 70% ethanol and gently resuspended in 0.5× TE. 12 µg of DNA was treated with 0.3 unit of Sau3A per µg of DNA at 37° C. in a volume of 100 µl. Samples were taken at 2-min intervals for 10 minutes. Then ¹/₁₀ volume 10× TE was added and samples were then heated for 30 minutes at 65° C. to inactivate the enzyme. The samples were subjected to electrophoresis to determine which fraction was in the 40-kb range and this sample was used in the ligation.

SuperCos cosmid vector (Stratagene, La Jolla, Calif.) was prepared as described by the supplier utilizing the BamHI cloning site. Prepared SuperCos at 100 ηg/ml was ligated with the AB1183 DNA previously digested with Sau3A at a ratio of 2:1 in a 5 µl volume overnight at 6° C. The ligation mixture was packaged using Gigapack XL III (Stratagene) as described by the supplier. Packaged phages were infected into XL-1MR *E. coli* cells (Stratagene) as described by the supplier. The cosmid library was plated on L-agar with 50 µg/ml kanamycin and incubated 16 hours at 37° C. 1200 colonies were picked and grown for testing against insects.

Example 2

Bioassay of Cosmid Clones

The 1200 colonies from Example 1 were screened for insecticidal activity against *Heliothis virescens* neonate larvae. The bioassay was performed using a surface contamination method on artificial diet. The bioassay was scored after 7 days. Eight clones were found to be insecticidal to *Heliothis virescens*.

Example 3

Analysis of Insecticidal Cosmid Clones

To identify vip3 homologous sequences, PCR analysis was performed on the eight *Heliothis virescens*-positive clones using primers from the 5' prime region of the vip3A gene (SEQ ID NO: 4), using the methods of Carozzi et al. (1991, Appl. Env. Microbiol. 57: 3057-3061). The primers used for this analysis are:

```
Forward:
                                    (SEQ ID NO: 8)
5'-GTGATCTAACCCTAGACG-3'

Reverse:
                                    (SEQ ID NO: 9)
5'-GCTTTAGTTCCATTCACTCC-3'.
```

One clone produced a DNA band of the size expected for genes related to the vip3 class. A 3.8 kb EcoRI fragment from this clone was subcloned into pBluescript (Stratagene) and transformed into *E. coli*. This *E. coli* clone was confirmed to comprise a vip3 homologous coding sequence using PCR analysis. The vip3 homologous coding sequence was designated vip3B. Bioassay results of the *E. coli* clone comprising the vip3B coding sequence demonstrated that the Vip3B toxin was responsible for the *Heliothis virescens* activity. The plasmid comprised in this clone, and the clone, were designated pCIB9400.

Example 4

Cloning and Sequencing the Full-Length Vip3B Gene pCIB9400 was cut with BglII and EcoRV to remove approximately 800 bp of flanking sequence near the 3' end of the vip3B coding sequence. The ends of the resulting fragment were filled in using Klenow polymerase (New England Biolabs, Beverly, Mass.) and then ligated together using T4 ligase (New England Biolabs, Beverly, Mass.) This ligation mixture was transformed into *E. coli* DH5α cells. Plasmid DNA was isolated from single colonies using a standard alkaline lysis procedure and several restriction digests were done to ensure that the 800 bp flanking region was deleted. The resulting plasmid was designated pNOV 1325 and deposited in *E. coli* as ATCC accession no. PTA-3868.

Sequencing was performed using the dideoxy chain-termination method and was completed using Applied Biosystems Inc. model 3700 automated DNA sequencer (Foster City, Calif.). The sequence was assembled using Sequencher 4.05 from Gene Codes Corporation (Ann Arbor, Mich.).

Sequence analysis identified a 2364 bp coding sequence (SEQ ID NO: 1) coding for a 787 amino acid protein (SEQ ID NO: 2) with an approximate molecular weight of 88 kDa. The vip3B nucleotide sequence has 86% identity to the nucleotide sequence of the vip3A gene. The amino acid sequence of the Vip3B protein is 81% identical to the amino acid sequence of the Vip3A protein.

Example 5

Bioassay of the Vip3B Protein Expressed in pNOV1325 and pCIB9400

Molten black cutworm diet (BioServ, Frenchtown, N.J.) was poured into 50 mm petri dishes and allowed to solidify. A 200 µl suspension of Top 10 (Invitrogen,) *E. coli* cells comprising either pNOV 1325 or pNOV9400 (each of which comprise the vip3B coding sequence) was pipetted onto the diet surface. The solution was uniformly spread with a bacterial loop so that the suspension covered the entire surface of the diet. The surface was allowed to dry thoroughly. First instar larvae of a lepidopteran species listed in the table below were placed on the diet with a fine tip brush. Each species was tested separately. Larval mortality was recorded at 3 days and 5 days after larval infestation of the diet. A sample containing Top10 *E. coli* cells without a vector was used for the negative control. Vip3A protein can also be tested in the same bioassay for comparative purposes. For this example, the Vip3B data obtained in this example were compared with the known activity spectrum data of Vip3A.

The bioassay results are shown in Table 1. Data shown in table 1 are from the day 5 post-infestation recording. Little or no activity was observed in the *E. coli* negative control. Results indicate that the Vip3B toxin has a broader spectrum of activity than the Vip3A toxin since Vip3B was active against *Ostrinia nubilalis* and *Plutella xylostella*. Results also suggest that Vip3B has a higher specific activity to *Helicoverpa zea* than the Vip3A toxin.

TABLE 1

| Insect | Percent Mortality | | E. coli Control | Activity Spectrum of Vip3A[b] |
|---|---|---|---|---|
| | pCIB9400 | pNOV1325 | | |
| Manduca sexta | 100 | 100 | 0 | + |
| Agrotis ipsilon | 100 | 100 | 5 | + |
| Helicoverpa zea | 100 | 100 | 10 | + |
| Heliothis virescens | 100 | 100 | 10 | + |
| Spodoptera exguia | 100 | 90 | 10 | + |
| Spodoptera frugiperda | 100 | 100 | 0 | + |
| Ostrinia nubilalis | 100 | 100 | 0 | − |
| Plutella xylostella | 100 | 100 | 0 | − |
| Trichplusia ni | 100 | 100 | 0 | + |
| Pectinophora gossypiella | 50[a] | 50[a] | 0 | + |
| Cochyles hospes | 60[a] | 80[a] | 0 | + |

[a]Surviving insects were observed to have severe feeding and growth inhibition.
[b]A "+" indicates an insect species that is susceptible to Vip3A. A "−" indicates an insect species with little or no susceptibility of Vip3A.

Example 6

Construction of Maize Optimized Vip3B Coding Sequence

A synthetic maize-optimized vip3B coding sequence was made according to the procedure disclosed in U.S. Pat. No. 5,625,136. In this procedure, maize preferred codons, i.e., the single codon that most frequently encodes that amino acid in maize, are used. The maize preferred codon for a particular amino acid is derived from known gene sequences from maize. Maize codon usage for 28 genes from maize plants is found in Murray et al., Nucleic Acids Research 17:477-498 (1989). The synthetic vip3B coding sequence (SEQ ID NO: 3) was cloned into a pET101/D-Topo expression vector. The resulting vector, designated pNOV 1328, was transformed into E. coli DH5α cells and deposited as ATCC accession number PTA-3869.

Example 7

Creation of Transgenic Maize Plants Comprising a Vip3B Gene

The synthetic maize-optimized vip3B (SEQ ID NO: 3) coding sequence was chosen for transformation into maize plants. An expression cassette comprising the synthetic vip3B coding sequence was transferred to a suitable vector for Agrobacterium-mediated maize transformation. Three vectors were constructed for this example: (a) a vector comprising two vip3B expression cassettes, the first expression cassette comprising MTL:vip3B, and the second expression cassette comprising PEPC:vip3B, (b) a vector comprising CMP:vip3B, and (c) a vector comprising UbiP:vip3B. All vectors used in this example also comprise the phosphomannose isomerase (PMI) gene for selection of transgenic lines (Negrotto et al. (2000) Plant Cell Reports 19: 798-803).

All three vectors were individually transformed into maize. Transformation of immature maize embryos was performed essentially as described in Negrotto et al., 2000, Plant Cell Reports 19: 798-803. For this example, all media constituents were as described in Negrotto et al., supra. However, various media constituents known in the art may be substituted.

Agrobacterium strain LBA4404 (pSB1) containing the plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ Agrobacterium were suspended in LS-inf media supplemented with 100 μM As (Negrotto et al., (2000) Plant Cell Rep 19: 798-803). Bacteria were pre-induced in this medium for 30-60 minutes.

Immature embryos from A188 were excised from 8-12 day old ears into liquid LS-inf+100 μM As. Immature embryos form other maize germplasm can also be used. Embryos were rinsed once with fresh infection medium. Agrobacterium solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for approximately 10 days.

Immature embryos, producing embryogenic callus were transferred to LSD 1M0.5S medium. The cultures were selected on this medium for approximately 6 weeks with a subculture step at approximately 3 weeks. Surviving calli were transferred to Reg1 medium supplemented with mannose. Following culturing in the light (16 hour light/8 hour dark regiment), green tissues were then transferred to Reg2 medium without growth regulators and incubated for approximately 1-2 weeks. Plantlets were transferred to Magenta GA-7 boxes (Magenta Corp, Chicago Ill.) containing Reg3 medium and grown in the light. After approximately 2-3 weeks, plants were tested for the presence of the PMI gene and the vip3B gene by PCR. Positive plants from the PCR assay were transferred to the greenhouse and tested for resistance to lepidopteran pests.

Example 8

Analysis of Transgenic Maize Plants Expressing Vip3B

Insect Bioassays

Plants were sampled as they were being transplanted from Magenta GA-7 boxes into soil. Sampling consisted of cutting two small pieces of leaf (ca. 2-4 cm long) and placing each piece in a small petri dish. Negative controls were either transgenic plants that were PCR negative for the vip3B gene from the same transformation experiment, or from non-transgenic plants (of a similar size to test plants) that were being grown under similar growth conditions as the transgenics.

Leaf samples from each plant were inoculated with either European corn borer (Ostrinia nubilalis) or fall armyworm (Spodoptera frugiperda) by placing 10 first instar larvae onto each leaf piece. Petri dishes are then tightly sealed. Other suitable insect pests can also be used.

At approximately 3-4 days post inoculation, data was collected. The percent mortality of the larvae was calculated. Also, a visual damage rating of the leaf can be ascertained at the same time. Feeding damage is rated as high, moderate, low, or absent and given a numerical value of 3, 2, 1 or 0, respectively.

Results of the bioassay of the transgenic plants are shown in Table 2. Results indicate that transgenic maize plants comprising the vip3B gene and expressing the Vip3B protein, are insecticidal to European corn borer and fall armyworm.

TABLE 2

Efficacy of Trangenic Maize Plants Expressing Vip3B.

| Event | Promter: vip3B Construct | % FAW Mortality Per Plant[a] | % ECB Mortality Per Plant[b] |
|---|---|---|---|
| 118A | MTL: vip3B/ PEPC: vip3B | 100, 100, 100, 100, 100, 100, 100, 100, 100, 100, 100, 100, 100, 100, 100, 100, 100, 100, 100, 100, 100, 100, 100, 100, 100, 100, 100, 100 | 90, 100, 100, 90, 100, 100, 80, 100 100, 100, 100, 90, 90, 90, 100, 100 90, 100, 70, 80, 70, 100, 100, 100, 70, 100, 80, 80 |
| 121A | MTL: vip3B/ PEPC: vip3B | 90, 100, 100, 100, 100, 100, 100, 100, 100, 100, 100, 100, 100, 100, 100, 100, 100, 100, 100, 100, 100, 100, 100, 100, 100, 100, 100, 100, 100, 100 | 70, 80, 70, 90, 80, 80, 90, 80, 80, 90, 100, 100, 80, 90, 70, 90, 80, 100, 80, 100, 70, 80, 70, 70, 90, 100, 100, 90 90, 90, 90 |
| 142C | MTL: vip3B/ PEPC: vip3B | 100, 100, 100, 100, 100, 100, 100, 100, 100 | 80, 100, 90, 80, 90, 70, 70, 90, 90 |
| 145B | MTL: vip3B/ PEPC: vip3B | 100, 100, 100, 100, 100, 100, 100, 100, 100, 100, 100, 100, 100, 100, 100, 100, 100 | 80, 70, 90, 100, 70, 70, 100, 80, 80, 70, 100, 100, 100, 100, 70, 100, 90, 90, 90 |
| 89A | CMP: vip3B | 100, 100, 100, 100, 100, 100, 100, 100 | 100, 100, 100, 100, 100, 100, 100, 100 |
| 190A | CMP: vip3B | 100, 100, 100, 100, 100, 100, 100, 100 | 100, 80, 90, 80, 90, 100, 80, 100, 80 |

[a]FAW = fall armyworm
[b]ECB = European corn borer

ELISA Assay

Levels of Vip3B protein in various transgenic maize tissues were determined using an ELISA. ELISA analysis was done according to the method disclosed in U.S. Pat. No. 5,625,136. Results of the ELISA analysis are shown in Table 3.

TABLE 3

Vip3B Protein Levels in Transgenic Maize.

| | Mean Vip3B Protein Level in Specified Tissue (µg/mg soluble protein) | | | |
|---|---|---|---|---|
| Event | Leaf | Pith | Rind | Pollen |
| 118A | 20 ± 12 | .316 ± .240 | .686 ± .645 | 0 |
| 121A | 20 ± 19 | .523 ± .387 | .723 ± .343 | 0 |
| 142C | 18 ± 17 | 1.12 ± .770 | 3.75 ± 1.30 | 0 |
| 145B | 19 ± 13 | .720 ± .720 | 2.23 ± 2.0 | 0 |

Example 9

Hybrid Vip3 Toxins

Vip3B is toxic to *Ostrinia nubilalis* (European corn borer) and *Plutella xylostella* (diamond back moth), whereas a related Vip toxin, Vip3A, has little or no activity. Vip3B and Vip3A differ primarily in the C-terminal region of their respective amino acid sequences particularly in the region from amino acid 579 to amino acid 787 of SEQ ID NO: 2. In order to demonstrate that this C-terminal region of Vip3B is the portion of the Vip3B toxin that is sufficient for the activity against European corn borer and diamond back moth, a hybrid toxin comprising the C-terminal region of Vip3B, starting at amino acid number 579 and ending at amino acid number 787 of SEQ ID NO: 2, was joined in an amino to carboxy direction with the N-terminal region of Vip3A, starting at amino acid number 1 and ending at amino acid number 578 of SEQ ID NO: 5. The hybrid toxin was designated Vip3A-B (SEQ ID NO: 7).

The nucleic acid molecule encoding the Vip3A-B hybrid toxin was constructed using two steps of PCR with the following primers:

VIP3A-N:
(SEQ ID NO: 10)
5'-ATGACCAAGAATAATACTAAATTAAGCAC-3'

VIPfus4:
(SEQ ID NO: 11)
5'-TCCTTATGAACATATAAAGCTTTAGTTCCATT-3'

VIP3B-C:
(SEQ ID NO: 12)
5'-GGCGAATTCTCACTTAATCGAAAAATTCCGGAAATTTAT-3'

VIPfus3:
(SEQ ID NO: 13)
5'-AATGGAACTAAAGCTTTATATGTTCATAAGGA-3'

In the first PCR step, primers Vip3A-N (SEQ ID NO: 10) and Vipfus4 (SEQ ID NO: 11) were used to generate an approximately 1.7 kb fragment of the 5' end of the vip3A gene, encoding the N-terminal region, and primers Vip3B-C (SEQ ID NO: 12) and Vipfus3 (SEQ ID NO: 13) were used to generate an approximately 0.7 kb fragment of the 3' end of the vip3B gene encoding the C-terminal region. In the second PCR step, these two fragments were combined as the templates for primers Vip3A-N (SEQ ID NO: 10) and Vip3B-C (SEQ ID NO: 12) to generate an approximately 2.4 kb hybrid vip3A-vip3B gene, designated vip3A-B (SEQ ID NO: 6).

An *E. coli* clone expressing the hybrid Vip3A-B toxin was tested for insecticidal activity against fall armyworm and European corn borer using the method outlined in Example 5. Results of some of the bioassays suggested that the C-terminal region of Vip3B is sufficient to confer European corn borer activity on the hybrid toxin.

Example 10

In Vitro Recombination of Vip3 Genes by DNA Shuffling

One of the vip3 genes of the present invention, for example SEQ ID NO: 1, 3, or 6 is amplified by PCR. The resulting DNA fragment is digested by DNaseI treatment essentially as described in Stemmer et al., *PNAS* 91: 10747-10751 (1994), and the PCR primers are removed from the reaction mixture. A PCR reaction is carried out without primers and is followed by a PCR reaction with the primers, both as described in Stemmer et al. (1994). The resulting DNA fragments are cloned into pTRC99a (Pharmacia, Cat no: 27-5007-01) and transformed into *E. coli* strain SASX38 by electroporation using the Biorad Gene Pulser and the manufacturer's conditions. The transformed bacteria are grown on medium overnight and screened for insecticidal activity.

In a similar reaction, PCR-amplified DNA fragments comprising one of the vip3 genes described herein (SEQ ID NO: 1, 3, or 6, or mutants thereof), and PCR-amplified DNA fragments comprising at least one other of the vip3 genes described herein (or a mutant thereof) are recombined in vitro and resulting variants with improved insecticidal properties are recovered as described below.

In order to increase the diversity of the shuffled vip3 gene library, a vip3 gene or genes (called the primary genes) are shuffled using synthetic oligonucleotide shuffling. A plurality (e.g., 2, 5, 10, 20, 50, 75, or 100 or more) of oligonucleotides corresponding to at least one region of diversity are synthesized. These oligonucleotides can be shuffled directly, or can be recombined with one or more of the family of nucleic acids.

The oligonucleotide sequence can be taken from other vip3 genes called secondary genes. The secondary genes have a certain degree of homology to the primary genes. There are several ways to select parts of the secondary gene for the oligonucleotide synthesis. For example, portions of the secondary gene can be selected at random. The DNA shuffling process will select those oligonucleotides, which can be incorporated into the shuffled genes.

The selected portions can be any lengths as long as they are suitable to synthesize. The oligonucleotides can also be designed based on the homology between the primary and secondary genes. A certain degree of homology is necessary for crossover, which must occur among DNA fragments during the shuffling. At the same time, strong heterogeneity is desired for the diversity of the shuffled gene library. Furthermore, a specific portion of the secondary genes can be selected for the oligonucleotide synthesis based on the knowledge in the protein sequence and function relationship.

The present invention has disclosed that the C-terminal domain of Vip3B is in part responsible for spectrum of activity of the Vip3 toxins. When the insecticidal spectrum is modified by the current invention utilizing the DNA shuffling technology, the C-terminal region of the nucleotide sequence of the secondary genes can be selected as a target region for synthesizing oligonucleotides used in an oligonucleotide shuffling procedure.

Since the insecticidal activity of the Vip3 protein is dependent, at least in part, to the N-terminal region, the N-terminal region of the secondary genes can be selected for oligonucleotide shuffling for increased insecticidal activity.

Example 11

High-Throughput Screen for Insecticidal Activity

Shuffled vip3 gene libraries in either *E. coli* or *Bacillus thuringiensis* are screened for insecticidal activity. Colonies are picked with a Q-bot (Beckman), placed in growth media in a standard 96-well format and grown over night. Each clone is then layered onto the surface of an insect diet in 96-well format and the surface allowed to dry. Optionally, pools of transformed cells are added to each well to increase the number of clones that are tested in the initial screening round. For example, screening 100 clones per well and using 10,000 wells provides a screen of $10^6$ clones.

Several neonate larvae of a target insect, for example, *Heliothis virescens, Helicoverpa zea* or *Spodoptera frugiperda*, are added to each well. The plate is covered with an air permeable membrane that retains the larvae in the wells into which they were placed. After 5 days the wells are evaluated for amount of diet consumed and/or insect mortality. Clones in wells indicating that little or no diet is consumed and/or where high insect mortality is observed are chosen for further analysis. Several clones should be found to have enhanced activity against the target insect.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A hybrid toxin active against *Ostrinia nubilalis* (European corn borer), comprising in an amino- to carboxy-terminal direction an N-terminal region of a first Vip3 protein joined to a C-terminal region of a second Vip3 protein different from the first Vip3 protein, wherein the first Vip3 protein is not active against European corn borer, and wherein the C-terminal region comprises amino acids 579-787 of SEQ ID NO:2.

2. The hybrid toxin according to claim 1, wherein the first Vip3 protein is a Vip3A protein.

3. The hybrid toxin according to claim 2, wherein the Vip3A protein comprises SEQ ID NO:5.

4. The hybrid toxin according to claim 3, wherein the N-terminal region comprises amino acids 1-578 of SEQ ID NO:5.

5. The hybrid toxin according to claim 4, wherein the hybrid toxin comprises SEQ ID NO:7.

6. A composition comprising the hybrid toxin according to claim 1 and an acceptable agricultural carrier, wherein the composition is active against *Ostrinia nubilalis* (European corn borer).

7. A method of controlling *Ostrinia nubilalis* (European corn borer), comprising delivering to the European corn borer an effective amount of the hybrid toxin according to claim 1.

8. A hybrid toxin active against *Ostrinia nubilalis* (European corn borer) produced by the method comprising, transforming a host cell with a nucleic acid molecule comprising a promoter operably linked to a nucleotide sequence encoding the hybrid toxin of claim 1; growing the host cell under conditions which allow expression of the hybrid toxin; and recovering the hybrid toxin.

\* \* \* \* \*

SEQUENCE LISTING

```
<160> NUMBER OF SEQ ID NOS: 13

<210> SEQ ID NO 1
<211> LENGTH: 2364
<212> TYPE: DNA
<213> ORGANISM: Bacillus thuringiensis
<220> FEATURE:
<221> NAME/KEY: CDS
<222> LOCATION: (1)..(2364)
<223> OTHER INFORMATION: Native vip3B coding sequence

<400> SEQUENCE: 1 atg aac aag aat aat act aaa tta aac gca agg gcc tta ccg agt ttt      48
Met Asn Lys Asn Asn Thr Lys Leu Asn Ala Arg Ala Leu Pro Ser Phe
1               5                   10                  15 att gat tat ttt aat ggc att tat gga ttt gcc act ggt atc aaa gac      96
Ile Asp Tyr Phe Asn Gly Ile Tyr Gly Phe Ala Thr Gly Ile Lys Asp
            20                  25                  30
```

```
att atg aac atg att ttt aaa acg gat aca ggt gga aat cta acc cta    144
Ile Met Asn Met Ile Phe Lys Thr Asp Thr Gly Gly Asn Leu Thr Leu
         35                  40                  45 gac gaa att tta aaa aat cag cag tta tta aat gag att tct ggt aaa    192
Asp Glu Ile Leu Lys Asn Gln Gln Leu Leu Asn Glu Ile Ser Gly Lys
 50                  55                  60 ttg gat ggg gta aat ggg agc tta aac gat ctt atc gca cag gga aac    240
Leu Asp Gly Val Asn Gly Ser Leu Asn Asp Leu Ile Ala Gln Gly Asn
65                  70                  75                  80 tta aat aca gaa tta tct aag gaa atc tta aaa att gca aat gag cag    288
Leu Asn Thr Glu Leu Ser Lys Glu Ile Leu Lys Ile Ala Asn Glu Gln
                 85                  90                  95 aat caa gtc tta aat gat gtt aat aac aaa ctt aat gcg ata aat aca    336
Asn Gln Val Leu Asn Asp Val Asn Asn Lys Leu Asn Ala Ile Asn Thr
            100                 105                 110 atg ctt cac ata tat cta cct aaa att aca tct atg tta aat gat gta    384
Met Leu His Ile Tyr Leu Pro Lys Ile Thr Ser Met Leu Asn Asp Val
            115                 120                 125 atg aaa caa aat tat gca cta agt ctg caa ata gaa tac cta agt aaa    432
Met Lys Gln Asn Tyr Ala Leu Ser Leu Gln Ile Glu Tyr Leu Ser Lys
130                 135                 140 caa ttg caa gaa att tcc gac aag tta gat gtc att aac gtg aat gta    480
Gln Leu Gln Glu Ile Ser Asp Lys Leu Asp Val Ile Asn Val Asn Val
145                 150                 155                 160 ctt att aac tct aca ctt act gaa att aca cct gcg tat caa cgg atg    528
Leu Ile Asn Ser Thr Leu Thr Glu Ile Thr Pro Ala Tyr Gln Arg Met
                165                 170                 175 aaa tat gta aat gaa aaa ttt gaa gat tta act ttt gct aca gaa acc    576
Lys Tyr Val Asn Glu Lys Phe Glu Asp Leu Thr Phe Ala Thr Glu Thr
            180                 185                 190 act tta aaa gta aaa aag aat agc tcc cct gca gat att ctt gat gag    624
Thr Leu Lys Val Lys Lys Asn Ser Ser Pro Ala Asp Ile Leu Asp Glu
            195                 200                 205 tta act gag tta act gaa cta gcg aaa agt gta aca aaa aat gac gtg    672
Leu Thr Glu Leu Thr Glu Leu Ala Lys Ser Val Thr Lys Asn Asp Val
210                 215                 220 gat ggt ttt gaa ttt tac ctt aat aca ttc cac gat gta atg gta gga    720
Asp Gly Phe Glu Phe Tyr Leu Asn Thr Phe His Asp Val Met Val Gly
225                 230                 235                 240 aac aat tta ttc ggg cgt tca gct tta aaa act gct tcg gaa tta atc    768
Asn Asn Leu Phe Gly Arg Ser Ala Leu Lys Thr Ala Ser Glu Leu Ile
                245                 250                 255 gct aaa gaa aat gtg aaa aca agt ggc agt gag gta gga aat gtt tat    816
Ala Lys Glu Asn Val Lys Thr Ser Gly Ser Glu Val Gly Asn Val Tyr
            260                 265                 270 aat ttc tta att gta tta aca gct ctg caa gca aaa gct ttt ctt act    864
Asn Phe Leu Ile Val Leu Thr Ala Leu Gln Ala Lys Ala Phe Leu Thr
            275                 280                 285 tta aca aca tgc cgg aaa tta tta ggc tta gca gat att gat tat act    912
Leu Thr Thr Cys Arg Lys Leu Leu Gly Leu Ala Asp Ile Asp Tyr Thr
            290                 295                 300 ttc att atg aat gaa cat tta gat aag gaa aaa gag gaa ttt aga gta    960
Phe Ile Met Asn Glu His Leu Asp Lys Glu Lys Glu Glu Phe Arg Val
305                 310                 315                 320 aat atc ctt cct aca ctt tct aat act ttt tct aat cct aac tat gca   1008
Asn Ile Leu Pro Thr Leu Ser Asn Thr Phe Ser Asn Pro Asn Tyr Ala
                325                 330                 335 aaa gct aaa gga agc aat gaa gat gca aag ata att gtg gaa gct aaa   1056
Lys Ala Lys Gly Ser Asn Glu Asp Ala Lys Ile Ile Val Glu Ala Lys
            340                 345                 350
```

```
cca gga tat gct ttg gtt gga ttt gaa atg agc aat gat tca atc aca    1104
Pro Gly Tyr Ala Leu Val Gly Phe Glu Met Ser Asn Asp Ser Ile Thr
        355                 360                 365 gta tta aaa gca tat cag gct aag cta aaa caa gat tat caa gtt gat    1152
Val Leu Lys Ala Tyr Gln Ala Lys Leu Lys Gln Asp Tyr Gln Val Asp
        370                 375                 380 aaa gat tcg tta tca gaa att gtc tat ggt gat atg gat aaa tta ttg    1200
Lys Asp Ser Leu Ser Glu Ile Val Tyr Gly Asp Met Asp Lys Leu Leu
385                 390                 395                 400 tgc ccg gat caa tct gaa caa ata tat tat aca aat aac att gct ttt    1248
Cys Pro Asp Gln Ser Glu Gln Ile Tyr Tyr Thr Asn Asn Ile Ala Phe
                405                 410                 415 ccc aat gaa tat gta att act aaa att act ttt act aaa aaa atg aat    1296
Pro Asn Glu Tyr Val Ile Thr Lys Ile Thr Phe Thr Lys Lys Met Asn
            420                 425                 430 agt tta aga tat gag gca aca gct aat ttt tat gat tct tct aca ggg    1344
Ser Leu Arg Tyr Glu Ala Thr Ala Asn Phe Tyr Asp Ser Ser Thr Gly
        435                 440                 445 gat att gat cta aat aag aca aaa gta gaa tca agt gaa gca gag tat    1392
Asp Ile Asp Leu Asn Lys Thr Lys Val Glu Ser Ser Glu Ala Glu Tyr
    450                 455                 460 agt acg cta agt gct agt act gat gga gtc tat atg ccg tta ggt att    1440
Ser Thr Leu Ser Ala Ser Thr Asp Gly Val Tyr Met Pro Leu Gly Ile
465                 470                 475                 480 atc agt gaa aca ttt ttg act cca att aat ggg ttt gga atc gta gtc    1488
Ile Ser Glu Thr Phe Leu Thr Pro Ile Asn Gly Phe Gly Ile Val Val
                485                 490                 495 gat gaa aat tca aaa tta gta aat tta aca tgt aaa tca tat tta aga    1536
Asp Glu Asn Ser Lys Leu Val Asn Leu Thr Cys Lys Ser Tyr Leu Arg
            500                 505                 510 gag gta tta tta gca aca gac tta agt aat aaa gaa act aaa ttg att    1584
Glu Val Leu Leu Ala Thr Asp Leu Ser Asn Lys Glu Thr Lys Leu Ile
        515                 520                 525 gtc cca cct att ggt ttt att agc aat att gta gaa aat ggg aac tta    1632
Val Pro Pro Ile Gly Phe Ile Ser Asn Ile Val Glu Asn Gly Asn Leu
    530                 535                 540 gag gga gaa aac tta gag ccg tgg aaa gca aat aac aaa aat gcg tat    1680
Glu Gly Glu Asn Leu Glu Pro Trp Lys Ala Asn Asn Lys Asn Ala Tyr
545                 550                 555                 560 gta gat cat aca ggc ggc gta aat gga act aaa gct tta tat gtt cat    1728
Val Asp His Thr Gly Gly Val Asn Gly Thr Lys Ala Leu Tyr Val His
                565                 570                 575 aag gat ggt gag ttt tca caa ttt att gga gat aag ttg aaa tcg aaa    1776
Lys Asp Gly Glu Phe Ser Gln Phe Ile Gly Asp Lys Leu Lys Ser Lys
            580                 585                 590 aca gaa tat gta att caa tat att gta aag gga aaa gct tct att ctt    1824
Thr Glu Tyr Val Ile Gln Tyr Ile Val Lys Gly Lys Ala Ser Ile Leu
        595                 600                 605 ttg aaa gat gaa aaa aat ggt gat tgc att tat gaa gat aca aat aat    1872
Leu Lys Asp Glu Lys Asn Gly Asp Cys Ile Tyr Glu Asp Thr Asn Asn
    610                 615                 620 ggt tta gaa gat ttt caa acc att act aaa agt ttt att aca gga acg    1920
Gly Leu Glu Asp Phe Gln Thr Ile Thr Lys Ser Phe Ile Thr Gly Thr
625                 630                 635                 640 gat tct tca gga gtt cat tta ata ttt aat agt caa aat ggc gat gaa    1968
Asp Ser Ser Gly Val His Leu Ile Phe Asn Ser Gln Asn Gly Asp Glu
                645                 650                 655 gca ttt ggg gaa aac ttt act att tca gaa att agg ctt tcc gaa gat    2016
Ala Phe Gly Glu Asn Phe Thr Ile Ser Glu Ile Arg Leu Ser Glu Asp
            660                 665                 670
```

```
tta tta agt cca gaa ttg ata aat tca gat gct tgg gtt gga tct cag   2064
Leu Leu Ser Pro Glu Leu Ile Asn Ser Asp Ala Trp Val Gly Ser Gln
        675                 680                 685 gga act tgg atc tca gga aat tca ctc act att aat agt aat gtg aat   2112
Gly Thr Trp Ile Ser Gly Asn Ser Leu Thr Ile Asn Ser Asn Val Asn
690                 695                 700 gga act ttt cga caa aac ctt tcg tta gaa agc tat tca act tat agt   2160
Gly Thr Phe Arg Gln Asn Leu Ser Leu Glu Ser Tyr Ser Thr Tyr Ser
705                 710                 715                 720 atg aac ttt aat gtg aat gga ttt gcc aag gtg aca gta aga aat tcc   2208
Met Asn Phe Asn Val Asn Gly Phe Ala Lys Val Thr Val Arg Asn Ser
                725                 730                 735 cgt gaa gta tta ttt gaa aaa aat tat ccg cag ctt tca cct aaa gat   2256
Arg Glu Val Leu Phe Glu Lys Asn Tyr Pro Gln Leu Ser Pro Lys Asp
            740                 745                 750 att tct gaa aaa ttc aca act gca gcc aat aat acc ggg ttg tat gta   2304
Ile Ser Glu Lys Phe Thr Thr Ala Ala Asn Asn Thr Gly Leu Tyr Val
        755                 760                 765 gag ctt tct cgt ttt aca tcg ggt ggc gct ata aat ttc cgg aat ttt   2352
Glu Leu Ser Arg Phe Thr Ser Gly Gly Ala Ile Asn Phe Arg Asn Phe
770                 775                 780 tcg att aag tga                                                   2364
Ser Ile Lys
785

<210> SEQ ID NO 2
<211> LENGTH: 787
<212> TYPE: PRT
<213> ORGANISM: Bacillus thuringiensis

<400> SEQUENCE: 2

Met Asn Lys Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asn Ala Ile Asn Thr
            100                 105                 110

Met Leu His Ile Tyr Leu Pro Lys Ile Thr Ser Met Leu Asn Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Met
                165                 170                 175

Lys Tyr Val Asn Glu Lys Phe Glu Asp Leu Thr Phe Ala Thr Glu Thr
            180                 185                 190

Thr Leu Lys Val Lys Lys Asn Ser Ser Pro Ala Asp Ile Leu Asp Glu
        195                 200                 205

Leu Thr Glu Leu Thr Glu Leu Ala Lys Ser Val Thr Lys Asn Asp Val
```

```
                    210                 215                 220
Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                    245                 250                 255

Ala Lys Glu Asn Val Lys Thr Ser Gly Ser Glu Val Gly Asn Val Tyr
                    260                 265                 270

Asn Phe Leu Ile Val Leu Thr Ala Leu Gln Ala Lys Ala Phe Leu Thr
                    275                 280                 285

Leu Thr Thr Cys Arg Lys Leu Leu Gly Leu Ala Asp Ile Asp Tyr Thr
                    290                 295                 300

Phe Ile Met Asn Glu His Leu Asp Lys Glu Lys Glu Glu Phe Arg Val
305                 310                 315                 320

Asn Ile Leu Pro Thr Leu Ser Asn Thr Phe Ser Asn Pro Asn Tyr Ala
                    325                 330                 335

Lys Ala Lys Gly Ser Asn Glu Asp Ala Lys Ile Ile Val Glu Ala Lys
                    340                 345                 350

Pro Gly Tyr Ala Leu Val Gly Phe Glu Met Ser Asn Asp Ser Ile Thr
                    355                 360                 365

Val Leu Lys Ala Tyr Gln Ala Lys Leu Lys Gln Asp Tyr Gln Val Asp
370                 375                 380

Lys Asp Ser Leu Ser Glu Ile Val Tyr Gly Asp Met Asp Lys Leu Leu
385                 390                 395                 400

Cys Pro Asp Gln Ser Glu Gln Ile Tyr Tyr Thr Asn Asn Ile Ala Phe
                    405                 410                 415

Pro Asn Glu Tyr Val Ile Thr Lys Ile Thr Phe Thr Lys Lys Met Asn
                    420                 425                 430

Ser Leu Arg Tyr Glu Ala Thr Ala Asn Phe Tyr Asp Ser Ser Thr Gly
                    435                 440                 445

Asp Ile Asp Leu Asn Lys Thr Lys Val Glu Ser Glu Ala Glu Tyr
                    450                 455                 460

Ser Thr Leu Ser Ala Ser Thr Asp Gly Val Tyr Met Pro Leu Gly Ile
465                 470                 475                 480

Ile Ser Glu Thr Phe Leu Thr Pro Ile Asn Gly Phe Gly Ile Val Val
                    485                 490                 495

Asp Glu Asn Ser Lys Leu Val Asn Leu Thr Cys Lys Ser Tyr Leu Arg
                    500                 505                 510

Glu Val Leu Leu Ala Thr Asp Leu Ser Asn Lys Glu Thr Lys Leu Ile
                    515                 520                 525

Val Pro Pro Ile Gly Phe Ile Ser Asn Ile Val Glu Asn Gly Asn Leu
530                 535                 540

Glu Gly Glu Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                    565                 570                 575

Lys Asp Gly Glu Phe Ser Gln Phe Ile Gly Asp Lys Leu Lys Ser Lys
                    580                 585                 590

Thr Glu Tyr Val Ile Gln Tyr Ile Val Lys Gly Lys Ala Ser Ile Leu
                    595                 600                 605

Leu Lys Asp Glu Lys Asn Gly Asp Cys Ile Tyr Glu Asp Thr Asn Asn
                    610                 615                 620

Gly Leu Glu Asp Phe Gln Thr Ile Thr Lys Ser Phe Ile Thr Gly Thr
625                 630                 635                 640
```

```
Asp Ser Ser Gly Val His Leu Ile Phe Asn Ser Gln Asn Gly Asp Glu
                645                 650                 655

Ala Phe Gly Glu Asn Phe Thr Ile Ser Glu Ile Arg Leu Ser Glu Asp
            660                 665                 670

Leu Leu Ser Pro Glu Leu Ile Asn Ser Asp Ala Trp Val Gly Ser Gln
        675                 680                 685

Gly Thr Trp Ile Ser Gly Asn Ser Leu Thr Ile Asn Ser Asn Val Asn
    690                 695                 700

Gly Thr Phe Arg Gln Asn Leu Ser Leu Glu Ser Tyr Ser Thr Tyr Ser
705                 710                 715                 720

Met Asn Phe Asn Val Asn Gly Phe Ala Lys Val Thr Val Arg Asn Ser
                725                 730                 735

Arg Glu Val Leu Phe Glu Lys Asn Tyr Pro Gln Leu Ser Pro Lys Asp
            740                 745                 750

Ile Ser Glu Lys Phe Thr Thr Ala Ala Asn Thr Gly Leu Tyr Val
        755                 760                 765

Glu Leu Ser Arg Phe Thr Ser Gly Gly Ala Ile Asn Phe Arg Asn Phe
    770                 775                 780

Ser Ile Lys
785
```

<210> SEQ ID NO 3
<211> LENGTH: 2364
<212> TYPE: DNA
<213> ORGANISM: Artificial Sequence
<220> FEATURE:
<223> OTHER INFORMATION: Chemically synthesized - Maize optimized vip3B
<220> FEATURE:
<221> NAME/KEY: misc_feature
<222> LOCATION: (1)..(2364)
<223> OTHER INFORMATION: Maize optimized vip3B

<400> SEQUENCE: 3

```
atgaacatga caacaccaa gctcaacgcc cgcgccctcc cgtccttcat cgactacttc      60
aacggcatct acggcttcgc caccggcatc aaggacatca tgaacatgat cttcaagacc     120
gacaccggcg gcaacctcac cctcgacgag atcctcaaga ccagcagct cctcaacgag      180 atttccggca agctcgacgg cgtgaacggc tccctcaacg acctcatcgc ccagggcaac     240
ctcaacaccg agctgtccaa ggagatcctc aagatcgcca acgagcagaa ccaggtgctc     300
aacgacgtga caacaagct caacgccatc aacaccatgc tccacatcta cctcccgaag      360
atcacctcca tgctcaacga cgtgatgaag cagaactacg ccctctcccct ccagatcgag    420 tacctctcca gcagctcca ggagatttcc gacaagctcg acgtgatcaa cgtgaacgtg      480
ctcatcaact ccaccctcac cgagatcacc ccggcctacc agcgcatgaa gtacgtgaac     540
gagaagttcg aggacctcac cttcgccacc gagaccaccc tcaaggtgaa gaagaactcc     600
tccccggccg acatcctcga cgagctgacc gagctgaccg agctggccaa gtccgtgacc     660
aagaacgacg tggacggctt cgagttctac ctcaacacct ccacgacgt gatggtgggc      720 aacaacctct cggccgctc cgccctcaag accgcctccg agctgatcgc caaggagaac      780
gtgaagacct ccggctccga ggtgggcaac gtgtacaact tcctcatcgt gctcaccgcc     840
ctccaggcca aggccttcct caccctcacc acctgccgca agctcctcgg cctcgccgac     900
atcgactaca ccttcatcat gaacgagcac ctcgacaagg agaaggagga gttccgcgtg     960
aacatcctcc cgaccctctc caacaccttc tccaacccga actacgccaa ggccaagggc    1020
tccaacgagg acgccaagat catcgtggag gccaagccgg gctacgccct cgtgggcttc    1080
```

```
gagatgtcca acgactccat caccgtgctc aaggcctacc aggccaagct caagcaggac    1140
taccaggtgg acaaggactc cctctccgag atcgtgtacg cgacatgga caagctcctc    1200 tgcccggacc agtccgagca aatctactac accaacaaca tcgccttccc gaacgagtac    1260
gtgatcacca agatcacctt caccaagaag atgaactccc tccgctacga ggccaccgcc    1320
aacttctacg actcctccac cggcgacatc gacctcaaca agaccaaggt ggagtcctcc    1380
gaggccgagt actccaccct ctccgcctcc accgacggcg tgtacatgcc gctcggcatc    1440
atctccgaga ccttcctcac cccgatcaac ggcttcggca tcgtggtgga cgagaactcc    1500
aagctcgtga acctcacctg caagtcctac ctccgcgagg tgctcctcgc caccgacctc    1560
tccaacaagg agaccaagct catcgtgccg ccgatcggct tcatctccaa catcgtggag    1620
aacggcaacc tggagggcga gaacctggag ccgtggaagg ccaacaacaa gaacgcctac    1680
gtggaccaca ccggcggcgt gaacggcacc aaggccctct acgtgcacaa ggacggcgag    1740
ttctcccagt tcatcggcga caagctcaag tccaagaccg agtacgtgat ccagtacatc    1800
gtgaagggca aggcctccat cctcctcaag gacgagaaga acggcgactg catctacgag    1860
gacaccaaca acgcctgga ggacttccag accatcacca gtccttcat caccggcacc    1920 gactcctccg gcgtgcacct catcttcaac tcccagaacg gcgacgaggc cttcggcgag    1980
aacttcacca tctccgagat ccgcctctcc gaggacctcc tctccccgga gctgatcaac    2040
tccgacgcct gggtgggctc ccagggcacc tggatctccg gcaactccct caccatcaac    2100
tccaacgtga acggcacctt ccgccagaac ctctccctgg agtcctactc cacctactcc    2160
atgaacttca acgtgaacgg cttcgccaag gtgaccgtgc gcaactcccg cgaggtgctc    2220
ttcgagaaga actacccgca gctctccccg aaggacatct ccgagaagtt caccaccgcc    2280
gccaacaaca ccggcctcta cgtggagctg tcccgcttca cctccggcgg cgccatcaac    2340
ttccgcaact tctccatcaa gtag                                          2364

<210> SEQ ID NO 4
<211> LENGTH: 2367
<212> TYPE: DNA
<213> ORGANISM: Bacillus thuringiensis
<220> FEATURE:
<221> NAME/KEY: CDS
<222> LOCATION: (1)..(2367)
<223> OTHER INFORMATION: Native vip3A coding sequence

<400> SEQUENCE: 4 atg aac aag aat aat act aaa tta agc aca aga gcc tta cca agt ttt      48
Met Asn Lys Asn Asn Thr Lys Leu Ser Thr Arg Ala Leu Pro Ser Phe
1               5                  10                  15 att gat tat ttt aat ggc att tat gga ttt gcc act ggt atc aaa gac     96
Ile Asp Tyr Phe Asn Gly Ile Tyr Gly Phe Ala Thr Gly Ile Lys Asp
            20                  25                  30 att atg aac atg att ttt aaa acg gat aca ggt ggt gat cta acc cta    144
Ile Met Asn Met Ile Phe Lys Thr Asp Thr Gly Gly Asp Leu Thr Leu
        35                  40                  45 gac gaa att tta aag aat cag cag tta cta aat gat att tct ggt aaa    192
Asp Glu Ile Leu Lys Asn Gln Gln Leu Leu Asn Asp Ile Ser Gly Lys
    50                  55                  60 ttg gat ggg gtg aat gga agc tta aat gat ctt atc gca cag gga aac    240
Leu Asp Gly Val Asn Gly Ser Leu Asn Asp Leu Ile Ala Gln Gly Asn
65                  70                  75                  80 tta aat aca gaa tta tct aag gaa ata tta aaa att gca aat gaa caa    288
Leu Asn Thr Glu Leu Ser Lys Glu Ile Leu Lys Ile Ala Asn Glu Gln
                85                  90                  95
```

```
aat caa gtt tta aat gat gtt aat aac aaa ctc gat gcg ata aat acg      336
Asn Gln Val Leu Asn Asp Val Asn Asn Lys Leu Asp Ala Ile Asn Thr
            100                 105                 110 atg ctt cgg gta tat cta cct aaa att acc tct atg ttg agt gat gta      384
Met Leu Arg Val Tyr Leu Pro Lys Ile Thr Ser Met Leu Ser Asp Val
        115                 120                 125 atg aaa caa aat tat gcg cta agt ctg caa ata gaa tac tta agt aaa      432
Met Lys Gln Asn Tyr Ala Leu Ser Leu Gln Ile Glu Tyr Leu Ser Lys
    130                 135                 140 caa ttg caa gag att tct gat aag ttg gat att att aat gta aat gta      480
Gln Leu Gln Glu Ile Ser Asp Lys Leu Asp Ile Ile Asn Val Asn Val
145                 150                 155                 160 ctt att aac tct aca ctt act gaa att aca cct gcg tat caa agg att      528
Leu Ile Asn Ser Thr Leu Thr Glu Ile Thr Pro Ala Tyr Gln Arg Ile
                165                 170                 175 aaa tat gtg aac gaa aaa ttt gag gaa tta act ttt gct aca gaa act      576
Lys Tyr Val Asn Glu Lys Phe Glu Glu Leu Thr Phe Ala Thr Glu Thr
            180                 185                 190 agt tca aaa gta aaa aag gat ggc tct cct gca gat att ctt gat gag      624
Ser Ser Lys Val Lys Lys Asp Gly Ser Pro Ala Asp Ile Leu Asp Glu
        195                 200                 205 tta act gag tta act gaa cta gcg aaa agt gta aca aaa aat gat gtg      672
Leu Thr Glu Leu Thr Glu Leu Ala Lys Ser Val Thr Lys Asn Asp Val
    210                 215                 220 gat ggt ttt gaa ttt tac ctt aat aca ttc cac gat gta atg gta gga      720
Asp Gly Phe Glu Phe Tyr Leu Asn Thr Phe His Asp Val Met Val Gly
225                 230                 235                 240 aat aat tta ttc ggg cgt tca gct tta aaa act gca tcg gaa tta att      768
Asn Asn Leu Phe Gly Arg Ser Ala Leu Lys Thr Ala Ser Glu Leu Ile
                245                 250                 255 act aaa gaa aat gtg aaa aca agt ggc agt gag gtc gga aat gtt tat      816
Thr Lys Glu Asn Val Lys Thr Ser Gly Ser Glu Val Gly Asn Val Tyr
            260                 265                 270 aac ttc tta att gta tta aca gct ctg caa gca aaa gct ttt ctt act      864
Asn Phe Leu Ile Val Leu Thr Ala Leu Gln Ala Lys Ala Phe Leu Thr
        275                 280                 285 tta aca aca tgc cga aaa tta tta ggc tta gca gat att gat tat act      912
Leu Thr Thr Cys Arg Lys Leu Leu Gly Leu Ala Asp Ile Asp Tyr Thr
    290                 295                 300 tct att atg aat gaa cat tta aat aag gaa aaa gag gaa ttt aga gta      960
Ser Ile Met Asn Glu His Leu Asn Lys Glu Lys Glu Glu Phe Arg Val
305                 310                 315                 320 aac atc ctc cct aca ctt tct aat act ttt tct aat cct aat tat gca     1008
Asn Ile Leu Pro Thr Leu Ser Asn Thr Phe Ser Asn Pro Asn Tyr Ala
                325                 330                 335 aaa gtt aaa gga agt gat gaa gat gca aag atg att gtg gaa gct aaa     1056
Lys Val Lys Gly Ser Asp Glu Asp Ala Lys Met Ile Val Glu Ala Lys
            340                 345                 350 cca gga cat gca ttg att ggg ttt gaa att agt aat gat tca att aca     1104
Pro Gly His Ala Leu Ile Gly Phe Glu Ile Ser Asn Asp Ser Ile Thr
        355                 360                 365 gta tta aaa gta tat gag gct aag cta aaa caa aat tat caa gtc gat     1152
Val Leu Lys Val Tyr Glu Ala Lys Leu Lys Gln Asn Tyr Gln Val Asp
    370                 375                 380 aag gat tcc tta tcg gaa gtt att tat ggt gat atg gat aaa tta ttg     1200
Lys Asp Ser Leu Ser Glu Val Ile Tyr Gly Asp Met Asp Lys Leu Leu
385                 390                 395                 400 tgc cca gat caa tct gaa caa atc tat tat aca aat aac ata gta ttt     1248
Cys Pro Asp Gln Ser Glu Gln Ile Tyr Tyr Thr Asn Asn Ile Val Phe
                405                 410                 415
```

-continued

| | | |
|---|---|---|
| cca aat gaa tat gta att act aaa att gat ttc act aaa aaa atg aaa<br>Pro Asn Glu Tyr Val Ile Thr Lys Ile Asp Phe Thr Lys Lys Met Lys<br>                420                            425                        430 | 1296 | act tta aga tat gag gta aca gcg aat ttt tat gat tct tct aca gga      1344
Thr Leu Arg Tyr Glu Val Thr Ala Asn Phe Tyr Asp Ser Ser Thr Gly
            435                 440                 445 gaa att gac tta aat aag aaa aaa gta gaa tca agt gaa gcg gag tat      1392
Glu Ile Asp Leu Asn Lys Lys Lys Val Glu Ser Ser Glu Ala Glu Tyr
    450                 455                 460 aga acg tta agt gct aat gat gat ggg gtg tat atg ccg tta ggt gtc      1440
Arg Thr Leu Ser Ala Asn Asp Asp Gly Val Tyr Met Pro Leu Gly Val
465                 470                 475                 480 atc agt gaa aca ttt ttg act ccg att aat ggg ttt ggc ctc caa gct      1488
Ile Ser Glu Thr Phe Leu Thr Pro Ile Asn Gly Phe Gly Leu Gln Ala
                485                 490                 495 gat gaa aat tca aga tta att act tta aca tgt aaa tca tat tta aga      1536
Asp Glu Asn Ser Arg Leu Ile Thr Leu Thr Cys Lys Ser Tyr Leu Arg
            500                 505                 510 gaa cta ctg cta gca aca gac tta agc aat aaa gaa act aaa ttg atc      1584
Glu Leu Leu Leu Ala Thr Asp Leu Ser Asn Lys Glu Thr Lys Leu Ile
        515                 520                 525 gtc ccg cca agt ggt ttt att agc aat att gta gag aac ggg tcc ata      1632
Val Pro Pro Ser Gly Phe Ile Ser Asn Ile Val Glu Asn Gly Ser Ile
530                 535                 540 gaa gag gac aat tta gag ccg tgg aaa gca aat aat aag aat gcg tat      1680
Glu Glu Asp Asn Leu Glu Pro Trp Lys Ala Asn Asn Lys Asn Ala Tyr
545                 550                 555                 560 gta gat cat aca ggc gga gtg aat gga act aaa gct tta tat gtt cat      1728
Val Asp His Thr Gly Gly Val Asn Gly Thr Lys Ala Leu Tyr Val His
                565                 570                 575 aag gac gga gga att tca caa ttt att gga gat aag tta aaa ccg aaa      1776
Lys Asp Gly Gly Ile Ser Gln Phe Ile Gly Asp Lys Leu Lys Pro Lys
            580                 585                 590 act gag tat gta atc caa tat act gtt aaa gga aaa cct tct att cat      1824
Thr Glu Tyr Val Ile Gln Tyr Thr Val Lys Gly Lys Pro Ser Ile His
        595                 600                 605 tta aaa gat gaa aat act gga tat att cat tat gaa gat aca aat aat      1872
Leu Lys Asp Glu Asn Thr Gly Tyr Ile His Tyr Glu Asp Thr Asn Asn
610                 615                 620 aat tta gaa gat tat caa act att aat aaa cgt ttt act aca gga act      1920
Asn Leu Glu Asp Tyr Gln Thr Ile Asn Lys Arg Phe Thr Thr Gly Thr
625                 630                 635                 640 gat tta aag gga gtg tat tta att tta aaa agt caa aat gga gat gaa      1968
Asp Leu Lys Gly Val Tyr Leu Ile Leu Lys Ser Gln Asn Gly Asp Glu
                645                 650                 655 gct tgg gga gat aac ttt att att ttg gaa att agt cct tct gaa aag      2016
Ala Trp Gly Asp Asn Phe Ile Ile Leu Glu Ile Ser Pro Ser Glu Lys
            660                 665                 670 tta tta agt cca gaa tta att aat aca aat aat tgg acg agt acg gga      2064
Leu Leu Ser Pro Glu Leu Ile Asn Thr Asn Asn Trp Thr Ser Thr Gly
        675                 680                 685 tca act aat att agc ggt aat aca ctc act ctt tat cag gga gga cga      2112
Ser Thr Asn Ile Ser Gly Asn Thr Leu Thr Leu Tyr Gln Gly Gly Arg
690                 695                 700 ggg att cta aaa caa aac ctt caa tta gat agt ttt tca act tat aga      2160
Gly Ile Leu Lys Gln Asn Leu Gln Leu Asp Ser Phe Ser Thr Tyr Arg
705                 710                 715                 720 gtg tat ttt tct gtg tcc gga gat gct aat gta agg att aga aat tct      2208
Val Tyr Phe Ser Val Ser Gly Asp Ala Asn Val Arg Ile Arg Asn Ser
                725                 730                 735

```
agg gaa gtg tta ttt gaa aaa aga tat atg agc ggt gct aaa gat gtt    2256
Arg Glu Val Leu Phe Glu Lys Arg Tyr Met Ser Gly Ala Lys Asp Val
        740                 745                 750 tct gaa atg ttc act aca aaa ttt gag aaa gat aac ttt tat ata gag    2304
Ser Glu Met Phe Thr Thr Lys Phe Glu Lys Asp Asn Phe Tyr Ile Glu
755                 760                 765 ctt tct caa ggg aat aat tta tat ggt ggt cct att gta cat ttt tac    2352
Leu Ser Gln Gly Asn Asn Leu Tyr Gly Gly Pro Ile Val His Phe Tyr
770                 775                 780 gat gtc tct att aag                                                2367
Asp Val Ser Ile Lys
785

<210> SEQ ID NO 5
<211> LENGTH: 789
<212> TYPE: PRT
<213> ORGANISM: Bacillus thuringiensis

<400> SEQUENCE: 5

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300
```

```
Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Ile Gly Phe Glu Ile Ser Asn Asp Ser Ile Thr
                355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
            530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
            610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Trp Thr Ser Thr Gly
            675                 680                 685

Ser Thr Asn Ile Ser Gly Asn Thr Leu Thr Leu Tyr Gln Gly Gly Arg
                690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
```

```
                            725                 730                 735
Arg Glu Val Leu Phe Glu Lys Arg Tyr Met Ser Gly Ala Lys Asp Val
            740                 745                 750
Ser Glu Met Phe Thr Thr Lys Phe Glu Lys Asp Asn Phe Tyr Ile Glu
            755                 760                 765
Leu Ser Gln Gly Asn Asn Leu Tyr Gly Gly Pro Ile Val His Phe Tyr
            770                 775                 780
Asp Val Ser Ile Lys
785

<210> SEQ ID NO 6
<211> LENGTH: 2364
<212> TYPE: DNA
<213> ORGANISM: Artificial Sequence
<220> FEATURE:
<223> OTHER INFORMATION: Chemically synthesized - Hybrid vip3A-B(1734)
<220> FEATURE:
<221> NAME/KEY: CDS
<222> LOCATION: (1)..(2364)
<223> OTHER INFORMATION: Hybrid vip3A-B(1734)

<400> SEQUENCE: 6 atg aac aag aat aat act aaa tta agc aca aga gcc tta cca agt ttt      48
Met Asn Lys Asn Asn Thr Lys Leu Ser Thr Arg Ala Leu Pro Ser Phe
1               5                   10                  15

| | | |
|---|---|---|
| tta act gag tta act gaa cta gcg aaa agt gta aca aaa aat gat gtg<br>Leu Thr Glu Leu Thr Glu Leu Ala Lys Ser Val Thr Lys Asn Asp Val<br>210                   215                   220 | 672 |
| gat ggt ttt gaa ttt tac ctt aat aca ttc cac gat gta atg gta gga<br>Asp Gly Phe Glu Phe Tyr Leu Asn Thr Phe His Asp Val Met Val Gly<br>225                   230                   235                   240 | 720 |
| aat aat tta ttc ggg cgt tca gct tta aaa act gca tcg gaa tta att<br>Asn Asn Leu Phe Gly Arg Ser Ala Leu Lys Thr Ala Ser Glu Leu Ile<br>                 245                   250                   255 | 768 |
| act aaa gaa aat gtg aaa aca agt ggc agt gag gtc gga aat gtt tat<br>Thr Lys Glu Asn Val Lys Thr Ser Gly Ser Glu Val Gly Asn Val Tyr<br>260                   265                   270 | 816 |
| aac ttc tta att gta tta aca gct ctg caa gca aaa gct ttt ctt act<br>Asn Phe Leu Ile Val Leu Thr Ala Leu Gln Ala Lys Ala Phe Leu Thr<br>    275                   280                   285 | 864 |
| tta aca aca tgc cga aaa tta tta ggc tta gca gat att gat tat act<br>Leu Thr Thr Cys Arg Lys Leu Leu Gly Leu Ala Asp Ile Asp Tyr Thr<br>290                   295                   300 | 912 |
| tct att atg aat gaa cat tta aat aag gaa aaa gag gaa ttt aga gta<br>Ser Ile Met Asn Glu His Leu Asn Lys Glu Lys Glu Glu Phe Arg Val<br>305                   310                   315                   320 | 960 |
| aac atc ctc cct aca ctt tct aat act ttt tct aat cct aat tat gca<br>Asn Ile Leu Pro Thr Leu Ser Asn Thr Phe Ser Asn Pro Asn Tyr Ala<br>                 325                   330                   335 | 1008 |
| aaa gtt aaa gga agt gat gaa gat gca aag atg att gtg gaa gct aaa<br>Lys Val Lys Gly Ser Asp Glu Asp Ala Lys Met Ile Val Glu Ala Lys<br>340                   345                   350 | 1056 |
| cca gga cat gca ttg att ggg ttt gaa att agt aat gat tca att aca<br>Pro Gly His Ala Leu Ile Gly Phe Glu Ile Ser Asn Asp Ser Ile Thr<br>                 355                   360                   365 | 1104 |
| gta tta aaa gta tat gag gct aag cta aaa caa aat tat caa gtc gat<br>Val Leu Lys Val Tyr Glu Ala Lys Leu Lys Gln Asn Tyr Gln Val Asp<br>370                   375                   380 | 1152 |
| aag gat tcc tta tcg gaa gtt att tat ggt gat atg gat aaa tta ttg<br>Lys Asp Ser Leu Ser Glu Val Ile Tyr Gly Asp Met Asp Lys Leu Leu<br>385                   390                   395                   400 | 1200 |
| tgc cca gat caa tct gaa caa atc tat tat aca aat aac ata gta ttt<br>Cys Pro Asp Gln Ser Glu Gln Ile Tyr Tyr Thr Asn Asn Ile Val Phe<br>                 405                   410                   415 | 1248 |
| cca aat gaa tat gta att act aaa att gat ttc act aaa aaa atg aaa<br>Pro Asn Glu Tyr Val Ile Thr Lys Ile Asp Phe Thr Lys Lys Met Lys<br>                 420                   425                   430 | 1296 |
| act tta aga tat gag gta aca gcg aat ttt tat gat tct tct aca gga<br>Thr Leu Arg Tyr Glu Val Thr Ala Asn Phe Tyr Asp Ser Ser Thr Gly<br>                 435                   440                   445 | 1344 |
| gaa att gac tta aat aag aaa aaa gta gaa tca agt gaa gcg gag tat<br>Glu Ile Asp Leu Asn Lys Lys Lys Val Glu Ser Ser Glu Ala Glu Tyr<br>450                   455                   460 | 1392 |
| aga acg tta agt gct aat gat gat ggg gtg tat atg ccg tta ggt gtc<br>Arg Thr Leu Ser Ala Asn Asp Asp Gly Val Tyr Met Pro Leu Gly Val<br>465                   470                   475                   480 | 1440 |
| atc agt gaa aca ttt ttg act ccg att aat ggg ttt ggc ctc caa gct<br>Ile Ser Glu Thr Phe Leu Thr Pro Ile Asn Gly Phe Gly Leu Gln Ala<br>                 485                   490                   495 | 1488 |
| gat gaa aat tca aga tta att act tta aca tgt aaa tca tat tta aga<br>Asp Glu Asn Ser Arg Leu Ile Thr Leu Thr Cys Lys Ser Tyr Leu Arg<br>                 500                   505                   510 | 1536 |
| gaa cta ctg cta gca aca gac tta agc aat aaa gaa act aaa ttg atc<br>Glu Leu Leu Leu Ala Thr Asp Leu Ser Asn Lys Glu Thr Lys Leu Ile<br>                 515                   520                   525 | 1584 |

```
gtc ccg cca agt ggt ttt att agc aat att gta gag aac ggg tcc ata    1632
Val Pro Pro Ser Gly Phe Ile Ser Asn Ile Val Glu Asn Gly Ser Ile
    530                 535                 540 gaa gag gac aat tta gag ccg tgg aaa gca aat aat aag aat gcg tat    1680
Glu Glu Asp Asn Leu Glu Pro Trp Lys Ala Asn Asn Lys Asn Ala Tyr
545                 550                 555                 560 gta gat cat aca ggc gga gtg aat gga act aaa gct tta tat gtt cat    1728
Val Asp His Thr Gly Gly Val Asn Gly Thr Lys Ala Leu Tyr Val His
                565                 570                 575 aag gat ggt gag ttt tca caa ttt att gga gat aag ttg aaa tcg aaa    1776
Lys Asp Gly Glu Phe Ser Gln Phe Ile Gly Asp Lys Leu Lys Ser Lys
            580                 585                 590 aca gaa tat gta att caa tat att gta aag gga aaa gct tct att ctt    1824
Thr Glu Tyr Val Ile Gln Tyr Ile Val Lys Gly Lys Ala Ser Ile Leu
        595                 600                 605 ttg aaa gat gaa aaa aat ggt gat tgc att tat gaa gat aca aat aat    1872
Leu Lys Asp Glu Lys Asn Gly Asp Cys Ile Tyr Glu Asp Thr Asn Asn
    610                 615                 620 ggt tta gaa gat ttt caa acc att act aaa agt ttt att aca gga acg    1920
Gly Leu Glu Asp Phe Gln Thr Ile Thr Lys Ser Phe Ile Thr Gly Thr
625                 630                 635                 640 gat tct tca gga gtt cat tta ata ttt aat agt caa aat ggc gat gaa    1968
Asp Ser Ser Gly Val His Leu Ile Phe Asn Ser Gln Asn Gly Asp Glu
                645                 650                 655 gca ttt ggg gaa aac ttt act att tca gaa att agg ctt tcc gaa gat    2016
Ala Phe Gly Glu Asn Phe Thr Ile Ser Glu Ile Arg Leu Ser Glu Asp
            660                 665                 670 tta tta agt cca gaa ttg ata aat tca gat gct tgg gtt gga tct cag    2064
Leu Leu Ser Pro Glu Leu Ile Asn Ser Asp Ala Trp Val Gly Ser Gln
        675                 680                 685 gga act tgg atc tca gga aat tca ctc act att aat agt aat gtg aat    2112
Gly Thr Trp Ile Ser Gly Asn Ser Leu Thr Ile Asn Ser Asn Val Asn
    690                 695                 700 gga act ttt cga caa aac ctt tcg tta gaa agc tat tca act tat agt    2160
Gly Thr Phe Arg Gln Asn Leu Ser Leu Glu Ser Tyr Ser Thr Tyr Ser
705                 710                 715                 720 atg aac ttt aat gtg aat gga ttt gcc aag gtg aca gta aga aat tcc    2208
Met Asn Phe Asn Val Asn Gly Phe Ala Lys Val Thr Val Arg Asn Ser
                725                 730                 735 cgt gaa gta tta ttt gaa aaa aat tat ccg cag ctt tca cct aaa gat    2256
Arg Glu Val Leu Phe Glu Lys Asn Tyr Pro Gln Leu Ser Pro Lys Asp
            740                 745                 750 att tct gaa aaa ttc aca act gca gcc aat aat acc ggg ttg tat gta    2304
Ile Ser Glu Lys Phe Thr Thr Ala Ala Asn Asn Thr Gly Leu Tyr Val
        755                 760                 765 gag ctt tct cgt ttt aca tcg ggt ggc gct ata aat ttc cgg aat ttt    2352
Glu Leu Ser Arg Phe Thr Ser Gly Gly Ala Ile Asn Phe Arg Asn Phe
    770                 775                 780 tcg att aag tga                                                    2364
Ser Ile Lys
785
```

<210> SEQ ID NO 7
<211> LENGTH: 787
<212> TYPE: PRT
<213> ORGANISM: Artificial Sequence
<220> FEATURE:
<223> OTHER INFORMATION: Synthetic Construct

<400> SEQUENCE: 7

```
Met Asn Lys Asn Asn Thr Lys Leu Ser Thr Arg Ala Leu Pro Ser Phe
1               5                   10                  15
```

```
Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asp Leu Thr Leu
         35                  40                  45

Asp Glu Ile Leu Lys Asn Gln Gln Leu Leu Asn Asp Ile Ser Gly Lys
 50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
             100                 105                 110

Met Leu Arg Val Tyr Leu Pro Lys Ile Thr Ser Met Leu Ser Asp Val
             115                 120                 125

Met Lys Gln Asn Tyr Ala Leu Ser Leu Gln Ile Glu Tyr Leu Ser Lys
 130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                 165                 170                 175

Lys Tyr Val Asn Glu Lys Phe Glu Glu Leu Thr Phe Ala Thr Glu Thr
             180                 185                 190

Ser Ser Lys Val Lys Lys Asp Gly Ser Pro Ala Asp Ile Leu Asp Glu
         195                 200                 205

Leu Thr Glu Leu Thr Glu Leu Ala Lys Ser Val Thr Lys Asn Asp Val
 210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                 245                 250                 255

Thr Lys Glu Asn Val Lys Thr Ser Gly Ser Glu Val Gly Asn Val Tyr
             260                 265                 270

Asn Phe Leu Ile Val Leu Thr Ala Leu Gln Ala Lys Ala Phe Leu Thr
         275                 280                 285

Leu Thr Thr Cys Arg Lys Leu Leu Gly Leu Ala Asp Ile Asp Tyr Thr
 290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                 325                 330                 335

Lys Val Lys Gly Ser Asp Glu Asp Ala Lys Met Ile Val Glu Ala Lys
             340                 345                 350

Pro Gly His Ala Leu Ile Gly Phe Glu Ile Ser Asn Asp Ser Ile Thr
         355                 360                 365

Val Leu Lys Val Tyr Glu Ala Lys Leu Lys Gln Asn Tyr Gln Val Asp
 370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                 405                 410                 415

Pro Asn Glu Tyr Val Ile Thr Lys Ile Asp Phe Thr Lys Lys Met Lys
             420                 425                 430

Thr Leu Arg Tyr Glu Val Thr Ala Asn Phe Tyr Asp Ser Ser Thr Gly
```

```
                435                 440                 445
Glu Ile Asp Leu Asn Lys Lys Val Glu Ser Ser Glu Ala Glu Tyr
        450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Gly Ser Ile
        530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Glu Phe Ser Gln Phe Ile Gly Asp Lys Leu Lys Ser Lys
            580                 585                 590
Thr Glu Tyr Val Ile Gln Tyr Ile Val Lys Gly Lys Ala Ser Ile Leu
        595                 600                 605
Leu Lys Asp Glu Lys Asn Gly Asp Cys Ile Tyr Glu Asp Thr Asn Asn
        610                 615                 620
Gly Leu Glu Asp Phe Gln Thr Ile Thr Lys Ser Phe Ile Thr Gly Thr
625                 630                 635                 640
Asp Ser Ser Gly Val His Leu Ile Phe Asn Ser Gln Asn Gly Asp Glu
                645                 650                 655
Ala Phe Gly Glu Asn Phe Thr Ile Ser Glu Ile Arg Leu Ser Glu Asp
            660                 665                 670
Leu Leu Ser Pro Glu Leu Ile Asn Ser Asp Ala Trp Val Gly Ser Gln
        675                 680                 685
Gly Thr Trp Ile Ser Gly Asn Ser Leu Thr Ile Asn Ser Asn Val Asn
        690                 695                 700
Gly Thr Phe Arg Gln Asn Leu Ser Leu Glu Ser Tyr Ser Thr Tyr Ser
705                 710                 715                 720
Met Asn Phe Asn Val Asn Gly Phe Ala Lys Val Thr Val Arg Asn Ser
                725                 730                 735
Arg Glu Val Leu Phe Glu Lys Asn Tyr Pro Gln Leu Ser Pro Lys Asp
            740                 745                 750
Ile Ser Glu Lys Phe Thr Thr Ala Ala Asn Asn Thr Gly Leu Tyr Val
        755                 760                 765
Glu Leu Ser Arg Phe Thr Ser Gly Gly Ala Ile Asn Phe Arg Asn Phe
        770                 775                 780
Ser Ile Lys
785

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized - primer

<400> SEQUENCE: 8
gtgatctaac cctagacg                                                     18
```

-continued

```
<210> SEQ ID NO 9
<211> LENGTH: 20
<212> TYPE: DNA
<213> ORGANISM: Artificial Sequence
<220> FEATURE:
<223> OTHER INFORMATION: Chemically synthesized - primer

<400> SEQUENCE: 9
gctttagttc cattcactcc                                              20

<210> SEQ ID NO 10
<211> LENGTH: 29
<212> TYPE: DNA
<213> ORGANISM: Artificial Sequence
<220> FEATURE:
<223> OTHER INFORMATION: Chemcially synthesized - primer

<400> SEQUENCE: 10
atgaccaaga ataatactaa attaagcac                                    29

<210> SEQ ID NO 11
<211> LENGTH: 32
<212> TYPE: DNA
<213> ORGANISM: Artificial Sequence
<220> FEATURE:
<223> OTHER INFORMATION: Chemically synthesized - primer

<400> SEQUENCE: 11
tccttatgaa catataaagc tttagttcca tt                                32

<210> SEQ ID NO 12
<211> LENGTH: 39
<212> TYPE: DNA
<213> ORGANISM: Artificial Sequence
<220> FEATURE:
<223> OTHER INFORMATION: Chemically synthesized - primer

<400> SEQUENCE: 12
ggcgaattct cacttaatcg aaaaattccg gaaatttat                         39

<210> SEQ ID NO 13
<211> LENGTH: 32
<212> TYPE: DNA
<213> ORGANISM: Artificial Sequence
<220> FEATURE:
<223> OTHER INFORMATION: Chemically synthesized - primer

<400> SEQUENCE: 13
aatggaacta aagctttata tgttcataag ga                                32
```